(12) United States Patent
Nakatsuka et al.

(10) Patent No.: US 11,737,957 B2
(45) Date of Patent: *Aug. 29, 2023

(54) DENTAL CURABLE COMPOSITION INCLUDING CHAIN TRANSFER AGENT

(71) Applicant: SHOFU INC., Kyoto (JP)

(72) Inventors: Toshiyuki Nakatsuka, Kyoto (JP); Toshio Kitamura, Kyoto (JP); Masanori Goto, Kyoto (JP); Tomohiro Kai, Kyoto (JP); Satoshi Takano, Kyoto (JP); Yoshiyuki Jogetsu, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,044

(22) Filed: Aug. 30, 2018

(65) Prior Publication Data

US 2018/0369076 A1 Dec. 27, 2018

Related U.S. Application Data

(62) Division of application No. 14/737,763, filed on Jun. 12, 2015, now Pat. No. 10,085,923.

(30) Foreign Application Priority Data

| Jul. 3, 2014 | (JP) | 2014-137944 |
| Jul. 3, 2014 | (JP) | 2014-137947 |
| Jul. 3, 2014 | (JP) | 2014-137948 |
| Jul. 3, 2014 | (JP) | 2014-137950 |
| Sep. 24, 2014 | (JP) | 2014-193776 |

(51) Int. Cl.
| *A61K 6/00* | (2020.01) |
| *A61C 13/087* | (2006.01) |
| *C08K 9/02* | (2006.01) |
| *C08L 33/04* | (2006.01) |
| *A61K 6/887* | (2020.01) |
| *A61K 6/60* | (2020.01) |
| *A61K 6/76* | (2020.01) |

(52) U.S. Cl.
CPC ............ *A61K 6/887* (2020.01); *A61C 13/087* (2013.01); *A61K 6/60* (2020.01); *A61K 6/76* (2020.01); *C08K 9/02* (2013.01)

(58) Field of Classification Search
None
See application file for complete search history.

(56) References Cited

U.S. PATENT DOCUMENTS

| 3,471,596 A * | 10/1969 | Petner et al. | C08L 25/08 |
| | | | 264/19 |
| 3,751,399 A * | 8/1973 | Lee, Jr. et al. | C08F 20/20 |
| | | | 526/232 |
| 4,490,497 A | 12/1984 | Evrard et al. | |
| 5,718,585 A | 2/1998 | Dehoff et al. | |
| 5,990,195 A | 11/1999 | Arita | |
| 6,221,931 B1 * | 4/2001 | Sakuma | A61K 6/0276 |
| | | | 428/404 |
| 8,501,834 B2 * | 8/2013 | Maletz | A61K 6/083 |
| | | | 522/13 |
| 10,085,923 B2 * | 10/2018 | Nakatsuka | A61K 6/0047 |
| 10,172,695 B2 * | 1/2019 | Okada | A61C 13/0004 |
| 2003/0050359 A1 | 3/2003 | Kimura | |
| 2005/0059751 A1 * | 3/2005 | Erdrich | A61K 6/083 |
| | | | 523/113 |
| 2007/0142495 A1 | 6/2007 | Neffgen et al. | |
| 2010/0016466 A1 | 1/2010 | Lueck | |
| 2010/0112518 A1 | 5/2010 | Engelbrecht | |
| 2011/0250558 A1 | 10/2011 | Maletz | |
| 2011/0263739 A1 | 10/2011 | Chisholm | |
| 2013/0289195 A1 | 10/2013 | Nagelsdiek | |
| 2014/0256850 A1 * | 9/2014 | Gerard | C08J 5/24 |
| | | | 523/222 |

FOREIGN PATENT DOCUMENTS

| DE | 4233886 | 3/1994 |
| EP | 0 591 716 | 9/1993 |
| JP | 62-48647 | 10/1987 |

(Continued)

OTHER PUBLICATIONS

Office Action dated Jan. 14, 2015 in corresponding Japanese Patent Application No. 2014-193776 (English translation).
Extended European Search Report dated Dec. 17, 2015 in corresponding European Patent Application No. 15171697.4.
The First Office Action dated Feb. 26, 2019 in corresponding Chinese Application No. 201510341555.7, with English translation.
Examination Report dated May 16, 2018 in corresponding Indian Application No. 3039/CHE/2015, with English translation.
Office Action dated Mar. 30, 2021, in corresponding Korean Patent Application No. 10-2015-0084014, with English translation.

*Primary Examiner* — Tae H Yoon

(74) *Attorney, Agent, or Firm* — Wenderoth, Lind & Ponack, L.L.P.

(57) ABSTRACT

A dental curable composition capable of use as a dental material that can substitute part or all of a natural tooth, in particular, a resin material for dental cutting and machining in the field of dental care. When a block shape usable as the resin material is produced, while mechanical properties and aesthetic properties required for a crown prosthetic appliance are maintained, the dental curable composition can be molded and processed with pressure and heating while strain generated in the block is reduced and no cracks and chipping occur. The dental curable composition includes (a) a polymerizable monomer and (b) a filler in a weight ratio of 10:90 to 70:30, and 0.01 to 10 parts by weight of (c) a polymerization initiator and 0.001 to 1 part by weight of (d) a chain transfer agent being a terpenoid compound based on 100 parts by weight of the polymerizable monomer (a).

12 Claims, 1 Drawing Sheet

(56) References Cited

FOREIGN PATENT DOCUMENTS

| | | |
|---|---|---|
| JP | 2-40310 | 2/1990 |
| JP | 3-13208 | 2/1991 |
| JP | 6-74235 | 9/1994 |
| JP | 7-29982 | 4/1995 |
| JP | 9-103438 | 4/1997 |
| JP | 10-323353 | 12/1998 |
| JP | 2004-307767 | 11/2004 |
| JP | 2007-236465 | 9/2007 |
| JP | 2007-526270 | 9/2007 |
| JP | 2009-541375 | 11/2009 |
| JP | 2011-037726 | 2/2011 |
| JP | 2011-190254 | 9/2011 |
| JP | 2012-211279 | 11/2012 |
| JP | 2012-214398 | 11/2012 |
| JP | 2013-216599 | 10/2013 |
| WO | 2008/000313 | 1/2008 |
| WO | WO 2014/021343 A1 * | 2/2014 |

\* cited by examiner

FIG. 1 SIMULATED ARTIFICIAL TOOTH

FIG. 2 DIRECTION IN PRESSURE TEST

DENTAL CURABLE COMPOSITION INCLUDING CHAIN TRANSFER AGENT

BACKGROUND OF THE INVENTION

Field of the Invention

The present invention relates to a dental curable composition to be suitably used as a dental material that can substitute part or all of a natural tooth, or a resin material for dental cutting and machining, and a resin material for dental cutting and machining, a resin artificial tooth and a composite resin artificial tooth produced by the dental curable composition.

Description of the Related Art

A resin or a composite obtained by mixing a resin and an inorganic filler has been conventionally used with being molded into an artificial tooth in one treatment in the field of dentistry. In formation of the artificial tooth, the material of the artificial tooth has been filled in a mold and cured, but strain has been generated in curing to cause cracks and chipping to be generated.

In recent years, a dental CAD/CAM system has become widely used, and has enabled cutting and machining precisely so as to allow a prosthetic appliance to be produced. A resin block and a composite resin block, also having flexibility as a material to be cut and machined, are easy in occlusal adjustment and polishing operation at a restoration laboratory or chair side, and hardly damage an opposing tooth due to abrading of themselves, as compared with a ceramics block. Such a resin block and a composite resin block have been filled in a mold and cured as in the artificial tooth, however, strain has been generated in curing to cause cracks and chipping to be generated.

Japanese Patent Laid-Open No. 10-323353 discloses a dental resin material including a methacrylate or acrylate monomer and a thermal polymerization initiator. The (meth)acrylate monomer included in this dental resin material, however, has a high heat-curing reaction rate, therefore, for example, curing is rapidly initiated near a surface of a molded product, which is in contact with a mold, and volume shrinkage locally occurs due to polymerization of the monomer, and thus there is the following problem: strain is generated in a molded product to thereby cause cracks and chipping to occur and a uniform molded product cannot be obtained.

With respect to the resin block and the composite resin block, there has been a demand for a molding technique for producing a material for machining, having a large shape. A large molded product is difficult to produce as a uniform molded product with no incorporation of gas bubbles, the absence of strain, and no cracks and chips. In particular, methyl methacrylate is low in boiling point and high in polymerizability, therefore easily causes generation of strain and incorporation of gas bubbles due to foaming, and has also many problems in terms of productivity, for example, is required to be polymerized over a long time in order to be uniformly polymerized and cured.

Japanese Patent Laid-Open No. 2012-214398 discloses the following: polyethylene glycol dimethacrylate having a specific molecular weight can be contained in a specific amount to thereby provide a molded product without generation of cracks and chipping. A resin molded product uniformly thermally cured, however, cannot be obtained, and the following problem is caused: strain is still generated in a molded product to thereby cause cracks and chipping to be generated.

Japanese Patent Laid-Open No. 2011-037726 describes the invention of a bactericidal sealer for filling a root canal, in which terpinen-4-ol is compounded in order to impart the bactericidal effect.

National Publication of International Patent Application No. 2009-541375 and National Publication of International Patent Application No. 2007-526270 describe a dental material such as a material for an artificial tooth, in which terpinene is compounded as a stabilizer.

While a resin material for dental cutting and machining (resin block), having a large shape, for use in a temporary prosthetic appliance or a denture base is produced by admixing a powder material mainly including polymethyl methacrylate with a liquid material mainly including methyl methacrylate, and then filling the resulting admixture into a mold for molding and processing with pressure and heating, such an admixture has a high thermal conductivity and therefore a portion thereof, being present in the vicinity of the mold, starts to be rapidly polymerized. Therefore, the following problem is caused: strain is generated between the vicinity of the mold and the inside of the mold to cause cracks and chipping to be generated. In addition, since methyl methacrylate is a polymerizable monomer having a low boiling point, there is also the following problem: foaming occurs in the process of a rise in mold temperature to generate gas bubbles in a molded product.

A resin material for dental cutting and machining (composite resin block), for producing a temporary prosthetic appliance, a denture base or the like, has a filler such as a silica filler or an organic/inorganic composite filler compounded at a high density in order to exhibit aesthetic property and mechanical properties required for a crown prosthetic appliance. In this case, a material structure is adopted in which a polymerizable monomer is present around the filler with being polymerized for curing. While the composite resin block is produced by, for example, filling a paste-like dental curable composition including the filler and the polymerizable monomer into a mold for molding and processing with pressure and heating, the filler and the polymerizable monomer have a largely different thermal conductivity from each other, and therefore the following problem is caused: micro-strain is generated in the block to cause cracks and chipping. This is because the polymerizable monomer in which heat conducts quickly under pressure and heating for production of the block is rapidly polymerized. Moreover, in molding and processing in which the paste-like dental curable composition is pressurized and heated in the mold, while heat polymerization instantly progresses in the paste in the vicinity of the mold because of ease of conduction of heat, heat polymerization slowly progresses in the paste far from the mold and present near the inside of the mold, in which heat hardly conducts, as compared with the former case. Such ununiform progress of heat polymerization depending on the location of the paste causes the following problem: micro-strain is generated in the block to cause cracks and chipping. In addition, when the polymerizable monomer having a low boiling point, such as methyl methacrylate, is used, there is also the following problem: foaming occurs in the process of a rise in mold temperature to generate gas bubbles in a molded product.

The resin artificial tooth and the composite artificial tooth are made having a form similar to a natural tooth by stacking respective layers for polymerization and curing by a compression molding method in which raw materials for a paste-like admixture are filled in a mold and pressurized and heated, an injection molding method in which the admixture is injected as a raw material into a mold at a constant pressure, or the like. The difference in conduction of heat, however, is caused by, for example, ununiform component compositions and thicknesses of the layers stacked and hence the presence of a thinner portion and a thicker portion in the same layer, and furthermore the locational relationship (for example, the vicinity of the mold or the inside of the mold) from the mold in filling of the admixture into the mold. As a result, the rate of polymerization and curing is changed, and there is the following problem: micro/macro-strain is generated to cause defects such as partial shrinkage, cracking, clouding and chips in molding with pressure and heating. In addition, when the respective layers are sequentially stacked with polymerization and curing, there is also the following problem: adhesiveness between the layers is insufficient due to the influences of compatibility in pressure-welding of a raw material for providing a new layer with polymerization and curing, to the surface of the layer cured, and of the polymerization shrinkage stress in the polymerization and curing, and physical properties intended are not exhibited.

Furthermore, a monofunctional (meth)acrylate monomer to be mainly used as a component of the resin artificial tooth has a low boiling point and therefore is to be foamed by a rapid rise of temperature to cause gas bubbles to be easily incorporated in polymerization and curing. There are also many problems in terms of productivity, for example, polymerization and curing are required to be performed over a long period of time in order to achieve uniform polymerization and curing.

From the foregoing, an object of the present invention is to provide a dental curable composition in which, when a block-shaped or disc-shaped molded product usable as a resin material for dental cutting and machining is produced while mechanical properties such as hardness, bending strength and compressive strength as well as aesthetic property required for a temporary prosthetic appliance, a denture base and a crown prosthetic appliance are maintained, the dental curable composition can be molded and processed with pressure and heating while strain generated in the molded product is reduced, no cracks and chipping occur, and no gas bubbles are incorporated due to foaming.

Another object of the present invention is to provide a resin artificial tooth in which, during molding and processing with pressure and heating for replicating a form similar to a natural tooth while respective layers of the resin artificial tooth are stacked by polymerization and curing, uniform polymerization and curing are achieved with no influences of the component compositions of the respective layers, the thickness of a layer structure and the like, strain generated in the resin artificial tooth is reduced to thereby inhibit defects such as local shrinkage, cracking, clouding and chips from being generated, molding and processing under pressure and heating conditions that cause no gas bubbles to be incorporated due to foaming can be conducted, and the respective layers firmly adhere not to adversely affect material properties.

SUMMARY OF THE INVENTION

In order to solve the above problems, it has been found that, during processing and molding with pressure and heating for producing a block-shaped or disc-shaped molded product for use as a resin material for dental cutting and machining, the difference in heat conductivity among respective components included in a paste-like dental curable composition to be polymerized and cured by heat via a mold, and the difference in rate of polymerization in the molded product depending on the location which is the vicinity or inside of the mold cause micro/macro-strain to be generated and cause cracks and chipping, and that when a polymerizable monomer having a low boiling point is included, it is foamed in the molded product due to a rise in mold temperature to cause gas bubbles to be incorporated, leading to completion of the present invention.

In detail, the rate of heat polymerization of a polymerizable monomer that is high in heat conductivity among the components included in the dental curable composition and that starts to be rapidly polymerized by heat is decreased by addition of a chain transfer agent to thereby allow uniform heat polymerization to progress, thereby making it possible to suppress generation of micro/macro-strain to suppress cracks and chipping. Furthermore, addition of the chain transfer material can also suppress foaming of the polymerizable monomer having a low boiling point to thereby allow incorporation of gas bubbles to be suppressed, and also a further effect is exerted when a dental curable composition including a filler low in heat conductivity in a large amount is molded and processed with pressure and heating.

In order to solve the above problems, it has been found that, when a resin artificial tooth is provided by molding and processing for replicating a form similar to a natural tooth while respective layers are stacked by polymerization and curing, a chain transfer agent can be compounded as a component of the resin artificial tooth to thereby decrease the rate of polymerization and curing with no influences of the component compositions of the layers, the thickness of a layer structure, the locational relationship of a raw material in a mold, and the like to provide uniform polymerization and curing, also to reduce incorporation of gas bubbles due to foaming, and furthermore to allow the respective layers to firmly adhere, thereby resulting in reductions in various defects caused in molding, leading to completion of the present invention.

Specifically, provided is a dental curable composition including (a) a polymerizable monomer and (b) a filler in a weight ratio of 10:90 to 70:30, and including 0.01 to 10 parts by weight of (c) a polymerization initiator and 0.001 to 1 part by weight of (d) a chain transfer agent being a terpenoid compound based on 100 parts by weight of the polymerizable monomer (a).

The present invention provides a dental curable composition in which, when a block-shaped or disc-shaped molded product usable as a resin material for dental cutting and machining is produced while mechanical properties such as hardness, bending strength and compressive strength as well as aesthetic property required for a temporary prosthetic appliance, a denture base and a crown prosthetic appliance are maintained, the dental curable composition can be molded and processed with pressure and heating while strain generated in the molded product is reduced, no cracks and chipping occur, and no gas bubbles are incorporated due to foaming.

Micro/macro-strain in polymerization is alleviated, and therefore a resin material for dental cutting and machining, having no chipping and cracks and having any of various uniform shapes, can be produced. In the dental curable composition of the present invention, a chain transfer material is added to thereby allow heat polymerization to uniformly progress, therefore a filler can be compounded in the dental curable composition in a large amount, and mechanical properties such as hardness, bending strength and compressive strength as well as aesthetic property required for a crown prosthetic appliance can be stably exhibited at a high level.

In addition, in the dental curable composition of the present invention, even if the monofunctional polymerizable monomer having a low boiling point is included, the chain transfer agent is added to thereby allow polymerization and curing to progress uniformly and slowly, resulting in no foaming, and strain can also be alleviated to thereby allow a resin material for dental cutting and machining that is a uniform molded product without gas bubbles, chipping, cracks, and the like to be produced. Furthermore, the dental curable composition of the present invention is uniformly polymerized by addition of the chain transfer material, and therefore mechanical properties such as hardness, bending strength and compressive strength can be stably exhibited and can be maintained at a high level as compared with material properties of a temporary prosthetic appliance or a denture base produced at a chair side or technical side.

The resin artificial tooth of the present invention, although including a monofunctional (meth)acrylate monomer low in boiling point and high in polymerizability, can be obtained with uniform polymerization and curing by a decrease in the rate of polymerization and curing by the effect of the chain transfer agent. Thus, generation of strain and incorporation of gas bubbles due to foaming in polymerization and curing can be suppressed, and therefore defects such as local shrinkage, cracking, clouding, chips and gas bubbles can be reduced. Also when the resin artificial tooth is provided by molding and processing for replicating a form similar to a natural tooth while the respective layers are stacked for polymerization and curing, there is hardly affected by the thickness of a layer structure and the locational relationship of a raw material in a mold, and defects such as local shrinkage, cracking, clouding, chips and gas bubbles can be reduced.

While a composite resin layer forming the composite resin artificial tooth of the present invention includes a filler and a polymerizable monomer having a different thermal conductivity from each other, the effect of the chain transfer agent decreases the rate of polymerization and curing to impart uniform polymerization and curing, and therefore micro-strain generated at the interface between the filler and the polymerizable monomer can be suppressed to result in no occurrence of defects such as local shrinkage, cracking, clouding and chips. In addition, an acrylic resin layer forming the composite resin artificial tooth of the present invention mainly includes a resin component high in thermal conductivity and an organic filler, therefore polymerization and curing rapidly progress with pressure and heating, but the effect of the chain transfer agent decreases the rate of polymerization and curing to impart uniform polymerization and curing, and therefore micro-strain is hardly generated to result in no occurrence of defects such as local shrinkage, cracking, clouding and chips. Furthermore, a local difference in thickness is caused in the same layer, but the effect of the chain transfer agent decreases the rate of polymerization and curing to thereby impart uniform polymerization and curing with no influence of the thickness, resulting in no occurrence of defects such as local shrinkage, cracking, clouding and chips. In addition, the chain transfer agent is compounded to thereby allow the polymerizable monomer to be polymerized and cured at a low degree of polymerization. Therefore, when a raw material is placed on the cured layer and is polymerized and cured with pressure and heating to be stacked, wettability therebetween can be enhanced to provide firm adhesion between the layers. As a result, not only no defects such as local shrinkage, cracking, clouding and chips occur, but also excellent physical properties can be exhibited.

DETAILED DESCRIPTION OF THE PREFERRED EMBODIMENTS

Figure 1:
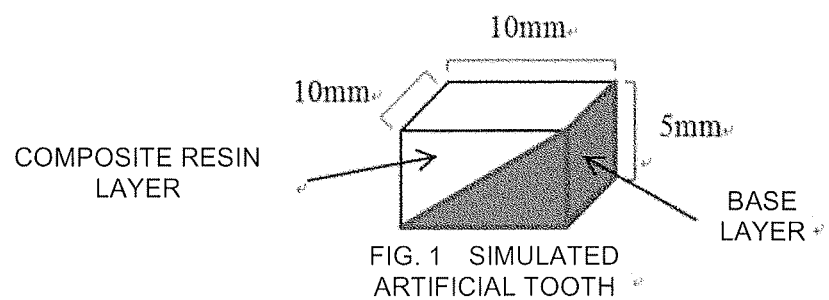
FIG. 1 illustrates a simulated artificial tooth used in a non-defective molded product test.

Hereinafter, the present invention is described in detail.

The present invention provides a dental curable composition including (a) a polymerizable monomer and (b) a filler in a weight ratio of 10:90 to 70:30, and including 0.01 to 10 parts by weight of (c) a polymerization initiator and 0.001 to 1 part by weight of (d) a chain transfer agent being a terpenoid compound based on 100 parts by weight of the polymerizable monomer (a).

In addition, a molded body of a resin material for dental cutting and machining produced by molding the dental curable composition of the present invention has a size of 1 to 350 $cm^3$, and can have a cubic shape, for example.

The polymerizable monomer (a) that can be used in the present invention can be any of known monofunctional and polyfunctional polymerizable monomers commonly used in the field of dentistry, without any limitation. Representative examples commonly suitably used include a (meth)acrylate monomer or a (meth)acryloyl polymerizable monomer having an acryloyl group and/or a methacryloyl group. In the present invention, the term "(meth)acrylate" or "(meth)acryloyl" inclusively refers to both of an acryloyl group-containing polymerizable monomer and a methacryloyl group-containing polymerizable monomer.

Specific examples of a (meth)acrylate polymerizable monomer that can be used as the polymerizable monomer (a) include the following.

Examples of a monofunctional monomer include (meth)acrylates such as methyl (meth)acrylate, ethyl (meth)acrylate, butyl (meth)acrylate (n-butyl (meth)acrylate, i-butyl (meth)acrylate), hexyl (meth)acrylate, dicyclopentenyl (meth)acrylate, tetrahydrofurfuryl (meth)acrylate, 2-hydroxyethyl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, methoxy polyethylene glycol (meth)acrylate, glycerol (meth)acrylate and isobornyl (meth)acrylate, silane compounds such as γ-(meth)acryloyloxypropyl trimethoxysilane and γ-(meth)acryloyloxypropyl triethoxysilane, and nitrogen-containing compounds such as 2-(N,N-dimethylamino) ethyl (meth)acrylate, N-methylol (meth)acrylamide and diacetone (meth)acrylamide.

Examples of an aromatic difunctional monomer include 2,2-bis(4-(meth)acryloyloxyphenyl)propane, 2,2-bis(4-(3-(meth)acryloyloxy-2-hydroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2(4-(meth)acryloyloxyethoxyphenyl)-2(4-(meth)acryloyloxydiethoxyphenyl)propane, 2(4-(meth)acryloyloxydiethoxyphenyl)-2(4-(meth)

acryloyloxytriethoxyphenyl)propane, 2(4-(meth)acryloyloxydipropoxyphenyl)-2(4-(meth) acryloyloxytriethoxyphenyl)propane, 2,2-bis(4-(meth) acryloyloxydipropoxyphenyl)propane and 2,2-bis(4-(meth) acryloyloxyisopropoxyphenyl)propane.

Examples of an aliphatic difunctional monomer include 2-hydroxy-3-acryloyloxypropyl methacrylate, hydroxypivalic acid neopentyl glycol di(meth)acrylate, ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, polyethylene glycol di(meth)acrylate, 1,3-butanediol di(meth)acrylate, 1,4-butanediol di(meth)acrylate, 1,6-hexanediol di(meth)acrylate and glycerol di(meth)acrylate.

Examples of a trifunctional monomer include trimethylolpropane tri(meth)acrylate, trimethylolethane tri(meth)acrylate, trimethylolmethane tri(meth)acrylate and pentaerythritol tri(meth)acrylate.

Examples of a tetrafunctional monomer include pentaerythritol tetra(meth)acrylate and ditrimethylolpropane tetra(meth)acrylate.

Examples of a urethane polymerizable monomer include difunctional, or tri- or higher functional urethane bond-containing di(meth)acrylates derived from an adduct of a polymerizable monomer having a hydroxy group, such as 2-hydroxyethyl (meth)acrylate, 2-hydroxypropyl (meth)acrylate or 3-chloro-2-hydroxypropyl (meth)acrylate, and a diisocyanate compound such as methylcyclohexane diisocyanate, methylene bis(4-cyclohexylisocyanate), hexamethylene diisocyanate, trimethylhexamethylene diisocyanate, isophorone diisocyanate, diisocyanate methyl methylbenzene or 4,4-diphenylmethane diisocyanate.

An oligomer or a prepolymer having at least one polymerizable group in its molecule may be used other than such a (meth)acrylate polymerizable monomer, without any limitation. There is no problem even if a substituent such as a fluoro group is contained in the same molecule.

The polymerizable monomers described above can be used not only singly but also in combinations of a plurality thereof.

When the dental curable composition of the present invention is used for producing a molded product, is used as a resin material for dental cutting and machining, or is used as a resin artificial tooth, a monofunctional polymerizable monomer having a boiling point of 50 to 200° C. is preferable among these monofunctional monomers. Specific examples of the monofunctional polymerizable monomer having a boiling point of 50 to 200° C. include methyl (meth)acrylate, ethyl (meth)acrylate, n-butyl (meth)acrylate, i-butyl (meth)acrylate, hexyl (meth)acrylate, dicyclopentenyl (meth)acrylate, 2-hydroxyethyl (meth)acrylate, benzyl (meth)acrylate and phenoxyethyl (meth)acrylate, but are not limited thereto. Among these monofunctional polymerizable monomers, methyl (meth)acrylate, ethyl (meth)acrylate or butyl (meth)acrylate having a boiling point in the range from 70 to 170° C. is preferably used, and methyl methacrylate or ethyl methacrylate having a boiling point in the range from 100 to 120° C. is more preferably used. Among these monofunctional polymerizable monomers, methyl methacrylate is preferably used.

These monofunctional polymerizable monomers can be used not only singly but also in combinations of a plurality thereof.

Herein, in the resin artificial tooth of the present invention, a monofunctional and/or polyfunctional polymerizable monomer other than the monofunctional polymerizable monomer having a boiling point of 50 to 200° C. can also be used in combination as long as it has no influences on production conditions for producing a block-shaped or disc-shaped molded product, conditions and material properties of the molded product, machining conditions in cutting and machining, and physical properties and molding processability of the resin artificial tooth. Representative examples commonly suitably used include a polymerizable monomer having an acryloyl group and/or a methacryloyl group, and for example, the above monofunctional monomer, aromatic difunctional monomer, aliphatic difunctional monomer, trifunctional monomer, tetrafunctional monomer and urethane polymerizable monomer can also be used in combination.

The content of the polymerizable monomer (a) that can be used in the dental curable composition of the present invention is not particularly limited, and the dental curable composition preferably includes the polymerizable monomer (a) and the filler (b) in a weight ratio of 10:90 to 70:30, more preferably in a ratio of 10:90 to 50:50, further preferably in a ratio of 20:80 to 40:60. When the weight ratio of the polymerizable monomer (a) to the filler (b) is less than 10:90, it is difficult to provide a composition in which the filler is uniformly dispersed, and when the weight ratio is more than 70:30, a sufficient mechanical strength cannot be achieved, and material properties are deteriorated, for example, surface hardness is reduced. With respect to the case where the filler (b) is a non-crosslinkable (meth)acrylate polymer, when the weight ratio of the polymerizable monomer (a) is less than 10, the non-crosslinkable (meth)acrylate polymer is not sufficiently swollen and a molded body cannot be obtained, and when the weight ratio of the polymerizable monomer (a) is more than 70, a resin component is included in a large amount to make it difficult to control a molding technique, for example, to increase the rate of polymerization and curing, and the following problem is found: sufficient physical properties are not achieved.

As the filler (b) that can be used in the present invention, a known filler commonly used in a dental composite material can be used. The filler (b) includes an inorganic filler, an organic filler and an organic/inorganic composite filler, and these fillers can be used not only singly but also in combinations of a plurality thereof regardless of the types of the fillers.

Specific examples of the inorganic filler include silica, aluminum silicate, alumina, titania, zirconia, various glasses (including fluoride glass, borosilicate glass, soda glass, barium glass, barium aluminum silica glass, glass including strontium or zirconium, glass ceramics, fluoroaluminosilicate glass, and synthetic glass by a sol-gel method), Aerosil (registered trademark), calcium fluoride, strontium fluoride, calcium carbonate, kaolin, clay, mica, aluminum sulfate, calcium sulfate, barium sulfate, titanium oxide, calcium phosphate, hydroxyapatite, calcium hydroxide, strontium hydroxide and zeolite. Such an inorganic filler may also be used as an aggregate, and examples of the aggregate include a silica-zirconia composite oxide aggregate obtained by mixing silica sol and zirconia sol and subjecting the mixture to spray drying and a heat treatment.

Examples of the organic filler include elastomers such as polyvinyl acetate, polyvinyl alcohol and a styrene-butadiene rubber, non-crosslinkable (meth)acrylate polymers each being a homopolymer of a monofunctional (meth)acrylate polymerizable monomer, such as polymethyl methacrylate (PMMA), polyethyl methacrylate, polypropyl methacrylate and polybutyl methacrylate, crosslinkable (meth)acrylate polymers obtained by copolymerizing a monofunctional (meth)acrylate polymerizable monomer with a polymerizable monomer having two or more functional groups, and polyvinyl acetate, polyethylene glycol, polypropylene glycol and polyvinyl alcohol, but are not limited thereto.

In addition, examples of the organic/inorganic composite filler include one obtained by covering the surface of a filler with a polymerizable monomer by polymerization, one obtained by mixing a filler and a polymerization monomer and polymerizing the monomer, and thereafter grinding the resultant to a proper particle size, or one obtained by dispersing a filler in a polymerizable monomer in advance for emulsion polymerization or suspension polymerization, but are not limited thereto at all.

As such a filler, a filler having any shape such as a spherical shape, a needle shape, a plate shape, a crushed shape or a scale shape can be used. The average particle size of the filler is different depending on the type of the filler, and in the case of the inorganic filler, any filler can be used as long as it has an average particle size in the range from 0.05 to 200 µm, preferably in the range from 0.5 to 100 µm, more preferably in the range from 1 to 20 µm. In the case of the organic/inorganic composite type filler, any filler can be used as long as it has an average particle size in the range from 0.05 to 150 µm, preferably in the range from 0.5 to 100 µm, more preferably in the range from 1 to 20 µm. Furthermore, in the case of the organic filler, the average particle size is not particularly limited, and any filler having an average particle size in any range can be used. Herein, the information on the average particle size can be examined by a laser diffraction type particle size measurement machine. When the filler (b) is an aggregate, the above average particle size corresponds to the average particle size of the aggregate. The average particle size of the filler is preferably in the range from 0.5 to 100 µm, more preferably in the range from 1 to 20 µm. Herein, the information on the average particle size and the variation coefficient of the particle size, and the like can be examined by a laser diffraction type particle size measurement machine, and when the filler (b) is an aggregate, the above average particle size corresponds to the average particle size of the aggregate. When the average particle size is less than 0.5 µm, the dental curable composition is sticky and gas bubbles are easily incorporated. When the average particle size is more than 100 µm, the filler (b) is easily precipitated in the composition and may not be uniformly dispersed.

The surface of the filler may also be multi-functionalized by a surface treatment method using a surface treatment agent, and the filler subjected to a surface treatment can be used without any limitation. Specific examples of the surface treatment agent for use in multi-functionalizing the surface of the filler include a surfactant, a fatty acid, an organic acid, an inorganic acid, various coupling materials (a titanate coupling agent, an aluminate coupling agent and a silane coupling agent), and a metal alkoxide compound. Specific examples of the surface treatment method include a method of spraying the surface treatment agent from above in the state of allowing the filler to flow, a method of dispersing the filler in a solution including the surface treatment agent, and a method of applying several surface treatment agents on the surface of the filler by a multilayer treatment. The surface treatment agent and the surface treatment method, however, are not limited thereto. Moreover, each of the surface treatment agent and the surface treatment method can be used singly or in combination compositely.

The content of the filler (b) that can be used in the present invention is not particularly limited, and the content thereof in the dental curable composition is preferably 30 to 90 parts by weight, more preferably 50 to 90 parts by weight. If the content of the filler (b) is less than 30 parts by weight, a sufficient mechanical strength cannot be achieved, and if the content is more than 90 parts by weight, it is difficult to provide a dental curable composition in, which the filler is uniformly dispersed.

In addition, the content of the filler (b) that can be used in a composite resin layer forming the composite resin artificial tooth of the present invention is not particularly limited, and the content thereof in the composite resin layer is preferably in the range from 30 to 90 parts by weight, more preferably in the range from 30 to 60 parts by weight. If the content of the filler is less than 30 parts by weight, material properties are deteriorated, for example, surface hardness is reduced, and on the other hand, if the content is more than 90 parts by weight, a resin component is contained in a small amount to deteriorate wettability between respective layers and not to impart sufficient adhesion, and therefore the problem of deterioration in material properties is caused.

Such a filler may be subjected to a surface treatment with a known titanate coupling agent, aluminate coupling agent or silane coupling agent without any problem. Examples of the silane coupling agent include γ-methacryloxypropyl trimethoxysilane and γ-methacryloxypropyl triethoxysilane. Preferably, γ-methacryloxypropyl trimethoxysilane is used. The aggregate and the filler may be subjected to a surface treatment with the same coupling agent or a different coupling agent.

In the dental curable composition of the present invention, when the polymerizable monomer (a) is the monofunctional polymerizable monomer having a boiling point of 50 to 200° C., a non-crosslinkable (meth)acrylate polymer is preferably used as the filler (b). The non-crosslinkable (meth)acrylate polymer is not particularly limited as long as it is swollen by the monofunctional polymerizable monomer, and a polymer obtained by homopolymerization of a (meth)acrylate polymerizable monomer, a polymer obtained by copolymerization of a plurality of such (meth)acrylate polymerizable monomers, a polymer obtained by copolymerization of the (meth) acrylate polymerizable monomer with another polymerizable monomer, or the like can be used therefor without any limitation. Specific examples of the non-crosslinkable (meth)acrylate polymer include homopolymers such as polymethyl (meth)acrylate, polyethyl (meth)acrylate, polypropyl (meth)acrylate, polyisopropyl (meth)acrylate, polyisobutyl (meth)acrylate and polybutyl (meth)acrylate, and copolymers of two or more among methyl (meth)acrylate, ethyl (meth)acrylate, propyl (meth)acrylate, isopropyl (meth)acrylate, isobutyl (meth)acrylate and butyl (meth) acrylate, but are not limited thereto. These non-crosslinkable (meth)acrylate polymers can be used not only singly but also in combinations of a plurality thereof. Among these non-crosslinkable (meth)acrylate polymers, polymethyl methacrylate, polyethyl methacrylate, or a copolymer of methyl methacrylate with ethyl methacrylate is preferably used. Polymethyl methacrylate is most preferably used.

The method for providing such a non-crosslinkable (meth)acrylate polymer by polymerization is not limited at all, and there is no problem even if the non-crosslinkable (meth)acrylate polymer is obtained by any polymerization method such as emulsion polymerization or suspension polymerization. The non-crosslinkable (meth)acrylate polymer can be used without any limitation, even if having any shape such as a spherical shape, a crushed shape or a hollow shape, but preferably a spherical shape. The non-crosslinkable (meth)acrylate polymer can be used without any limitation as long as the average particle size (50%) thereof is in the range from 1 to 300 µm, preferably in the range from 1 to 200 µm, further preferably in the range from 5 to 150 µm. The non-crosslinkable (meth)acrylate polymer can be used without any limitation as long as the weight average molecular weight thereof is in the range from 10000 to 2000000, preferably in the range from 50000 to 1500000, further preferably in the range from 100000 to 1500000.

In addition, any one can be used without any limitation, in which the surface of an organic filler, an inorganic filler, an organic/inorganic composite filler, an organic/inorganic compound, an organic/inorganic pigment or the like is subjected to secondary processing such as a surface modification treatment or a composite-forming treatment in which the surface is covered with the non-crosslinkable (meth)acrylate polymer.

The non-crosslinkable (meth)acrylate polymer for use in the dental curable composition of the present invention can be used without any limitation as long as the content thereof is in the range from 30 to 90 parts by weight, preferably in the range from 40 to 90 parts by weight, more preferably in the range from 50 to 90 parts by weight, further preferably in the range from 50 to 80 parts by weight, most preferably in the range from 60 to 80 parts by weight.

If the content of the non-crosslinkable (meth)acrylate polymer is less than 30 parts by weight, there is the problem of an excess of the monofunctional polymerizable monomer having a boiling point of 50 to 200° C. not to allow uniform swelling to occur. On the other hand, if the content is more than 90% by weight, there is the problem of an excess of the non-crosslinkable (meth)acrylate polymer not to allow uniform curing to occur, resulting in an ununiform product in molding. With respect to the case where the non-crosslinkable (meth)acrylate polymer is used for the resin artificial tooth, if the content of the non-crosslinkable (meth)acrylate polymer is less than 30 parts by weight, an excess of the monofunctional polymerizable monomer is present to increase the rate of polymerization and curing to adversely affect moldability, and sufficient physical properties cannot be achieved. On the other hand, if the content is more than 90 parts by weight, the monofunctional polymerizable monomer cannot allow an excessive amount of the non-crosslinkable (meth)acrylate polymer to be uniformly swollen, and the problem of moldability is caused.

Herein, a filler other than the non-crosslinkable (meth)acrylate polymer can be used as the filler (b) as long as it has no influences on physical properties, aesthetic property and moldability of the resin artificial tooth of the present invention. As such a filler, an organic component, an inorganic component, and a mixture or composite thereof can be used without any limitation as long as these do not allow the monofunctional (meth)acrylate polymerizable monomer to be swollen.

Specific examples of the filler other than the non-crosslinkable (meth)acrylate polymer include inorganic fillers including metal hydroxides such as aluminum hydroxide, calcium hydroxide and magnesium hydroxide, carbonates such as calcium carbonate and strontium carbonate, metal oxides such as aluminum oxide, metal fluorides such as barium fluoride, calcium fluoride and strontium fluoride, and talc, kaolin, clay, mica, hydroxyapatite, silica, quartz, and various glasses (glasses of sodium, heavy metals such as strontium, barium and lanthanum and/or fluorine-containing fluoroaluminosilicate, borosilicate, aluminoborate, fluoroalumino borosilicate, and the like), organic fillers including elastomers such as polyvinyl acetate, polyvinyl alcohol and a styrene-butadiene rubber, and a crosslinkable (meth)acrylate polymer obtained by copolymerization of a monofunctional (meth)acrylate polymerizable monomer with a polymerizable monomer having two or more functional groups, and organic/inorganic composite type fillers such as one in which the surface of an inorganic filler is covered by polymerization of a polymerizable monomer, one obtained by mixing an inorganic filler and a polymerization monomer and polymerizing the monomer, and thereafter grinding the resultant to a proper particle size, and one obtained by dispersing a filler in a polymerizable monomer in advance for emulsion polymerization or suspension polymerization, but are not limited thereto. These fillers can be used not only singly but also in combinations of a plurality thereof.

As the filler other than the non-crosslinkable (meth)acrylate polymer, a filler having any shape such as a spherical shape, a needle shape, a plate shape, a crushed shape or a scale shape can be used. The filler is not particularly limited as long as the average particle size (50%) thereof is in the range from 1 to 200 µm, preferably in the range from 5 to 100 µm, further preferably in the range from 10 to 80 µm.

The surface of the filler other than the non-crosslinkable (meth)acrylate polymer may be further multi-functionalized by a surface treatment method using a surface treatment agent or the like, and such a filler subjected to a surface treatment can also be used without any limitation. Specific examples of the surface treatment agent for use in multi-functionalizing the surface of the filler include a surfactant, a fatty acid, an organic acid, an inorganic acid, various coupling materials and a metal alkoxide compound. In addition, specific examples of the surface treatment method include a method of spraying the surface treatment agent from above in the state of allowing the filler to flow, a method of dispersing the filler in a solution including the surface treatment agent, and a method of applying several surface treatment agents on the surface of the filler by a multilayer treatment. The surface treatment agent and the surface treatment method, however, are not limited thereto. Moreover, each of the surface treatment agent and the surface treatment method can be used singly or in combination compositely.

The polymerization initiator (c) that can be used in the present invention is not particularly limited, and a known polymerization initiator, for example, a radical generator is used without any limitation. The polymerization initiator is roughly classified into an initiator that is mixed immediately before use to thereby initiate polymerization (chemical polymerization initiator), an initiator that initiates polymerization by heating or warming (heat polymerization initiator), and an initiator that initiates polymerization by irradiation with light (photo-polymerization initiator), and any polymerization initiator thereof can be used in the present invention without any limitation. These polymerization initiators can be used not only singly but also in combinations of a plurality thereof, regardless of the polymerization manner or the polymerization method. Furthermore, these polymerization initiators can be used without any problem, even if being subjected to a secondary treatment such as encapsulation in a microcapsule for the purposes of realizing stabilization of polymerization or delaying of polymerization. Among these polymerization initiators, a heat polymerization initiator is preferably used.

For the heat polymerization initiator, specifically, for example, organic peroxides such as benzoyl peroxide, p-chlorobenzoyl peroxide, 2,4-dichlorobenzoyl peroxide, acetyl peroxide, lauroyl peroxide, tert-butyl peroxide, cumene hydroperoxide, 2,5-dimethylhexane, 2,5-dihydroperoxide, methyl ethyl ketone peroxide and tert-butylperoxybenzoate, and azo compounds such as azobisisobutyronitrile, azobis(methyl isobutyrate) or azobiscyanovaleric acid are suitably used. Among them, organic peroxides are preferably used, more preferably benzoyl peroxide.

These polymerization initiators can be used without any limitation, even if subjected to secondary processing in order to control polymerization properties or ensure stability.

For the chemical polymerization initiator, a redox type polymerization initiation system of organic peroxide/amine compound, organic peroxide/amine compound/sulfinate, organic peroxide/amine compound/barbituric acid or barbituric acid derivative, or organic peroxide/amine compound/borate compound, an organometal polymerization initiator system in which a reaction with oxygen or water allows polymerization to be initiated, or the like is used. Sulfinates and borate compounds can be used because of being capable of reacting with a polymerizable monomer having an acidic group to thereby initiate polymerization.

Specific examples of the chemical polymerization initiator are shown below, but are not limited to the following.

Specific examples of the organic peroxide include benzoyl peroxide, p-chlorobenzoyl peroxide, 2,4-dichlorobenzoyl peroxide, acetyl peroxide, lauroyl peroxide, tert-butyl peroxide, cumene hydroperoxide, 2,5-dimethyl-2,5-di(benzoylperoxy)hexane, 2,5-dihydroperoxide, methyl ethyl ketone peroxide and tert-butylperoxybenzoate.

Specific examples of the amine compound preferably include a secondary or tertiary amine in which an amine group is bound to an aryl group, and specific examples include p-N,N-dimethyl-toluidine, N,N-dimethylaniline, N-β-hydroxyethyl-aniline, N,N-di(β-hydroxyethyl)-aniline, p-N,N-di(β-hydroxyethyl)-toluidine, N-methyl-aniline and p-N-methyl-toluidine.

Specific examples of the sulfonates include sodium benzenesulfinate, lithium benzenesulfinate and sodium p-toluenesulfinate.

Specific examples of the barbituric acid and derivatives thereof include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-5-tert-butylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-5-ethylbarbituric acid, 1-benzyl-5-phenylbarbituric acid and thiobarbituric acids, as well as salts thereof (particularly preferably alkali metal or alkaline-earth metal salts), for example, sodium 5-butylbarbiturate, sodium 1,3,5-trimethylbarbiturate, calcium 1,3,5-trimethylbarbiturate and sodium 1-cyclohexyl-5-ethylbarbiturate.

Specific examples of the borate compound include sodium salts, lithium salts, potassium salts, magnesium salts, tetrabutylammonium salts and tetramethylammonium salts of trialkylphenylboron and trialkyl(p-chlorophenyl) boron (an alkyl group is a n-butyl group, a n-octyl group, a n-dodecyl group or the like).

Furthermore, specific examples of the organometal polymerization initiator include organic boron compounds such as triphenylborane, tributylborane and tributylborane partial oxide.

Specific examples of perborate include sodium perborate, potassium perborate and ammonium perborate, specific examples of permanganate include ammonium permanganate, potassium permanganate and sodium permanganate, and furthermore specific examples of persulfate include ammonium persulfate, potassium persulfate and sodium persulfate. For the heat polymerization initiator by heating or warming, azo compounds such as azobisisobutyronitrile, azobis(methyl isobutyrate) and azobiscyanovaleric acid, other than the above organic peroxides, are suitably used.

For the photo-polymerization initiator, one made of a photosensitizer, for example, photosensitizer/photopolymerization promoter is used. Specific examples of the photopolymerization initiator are shown below, but are not limited to the following.

Specific examples of the photosensitizer include α-diketones such as benzyl, camphor quinone, α-naphthyl, acetonaphthene, p,p'-dimethoxybenzyl, p,p'-dichlorobenzylacetyl, pentanedione, 1,2-phenanthrenequinone, 1,4-phenanthrenequinone, 3,4-phenanthrenequinone, 9,10-phenanthrenequinone and naphthoquinone, benzoin alkyl ethers such as benzoin, benzoin methyl ether and benzoin ethyl ether, thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone, benzophenones such as benzophenone, p-chlorobenzophenone and p-methoxybenzophenone, acylphosphine oxides such as 2,4,6-trimethylbenzoyl diphenylphosphine oxide and bis(2,6-dimethoxybenzoyl)-2,4,4-trimethylpentylphosphine oxide, α-aminoacetophenones such as 2-benzyl-dimethylamino-1-(4-morpholinophenyl)-butanone-1,2-benzyl-diethylamino-1-(4-morpholinophenyl)-propanone-1, ketals such as benzyl dimethyl ketal, benzyl diethyl ketal and benzyl(2-methoxyethyl ketal), and titanocenes such as bis(cyclopentadienyl)-bis[2,6-difluoro-3-(1-pyrrolyl)phenyl]-titanium, bis(cyclopentadienyl)-bis(pentafluorophenyl)-titanium and bis(cyclopentadienyl)-bis(2,3,5,6-tetrafluoro-4-disiloxyphenyl)-titanium.

Specific examples of the photopolymerization promoter include tertiary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, p-N,N-dihydroxyethyl-toluidine, p-dimethylaminophenyl alcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino)diethanol, secondary amines such as N-phenylglycine, barbituric acids such as 5-butylbarbituric acid and 1-benzyl-5-phenylbarbituric acid, tin compounds such as dibutyl tin diacetate, dibutyl tin dilaurate, dioctyl tin dilaurate, dioctyl tin diversatate, a dioctyl tin bis(mercaptoacetic acid isooctyl ester) salt and tetramethyl-1,3-diacetoxydistannoxane, aldehyde compounds such as laurylaldehyde and terephthalaldehyde, and sulfur-containing compounds such as dodecylmercaptan, 2-mercaptobenzoxazole, 1-decanethiol and thiosalicylic acid.

In order to enhance photopolymerization promotion performances, it is effective to add, in addition to the above photopolymerization promoter, oxycarboxylic acids such as citric acid, malic acid, tartaric acid, glycolic acid, gluconic acid, α-oxyisobutyric acid, 2-hydroxypropanoic acid, 3-hydroxypropanoic acid, 3 hydroxybutanoic acid, 4-hydroxybutanoic acid and dimethylolpropionic acid.

These polymerization initiators can be used not only singly but also in combinations of two or more, regardless of the polymerization manner or the polymerization method. In addition, these polymerization initiators have no problem even if subjected to a secondary treatment such as encapsulation in a microcapsule, if necessary.

Such a polymerization initiator is used in production of the non-crosslinkable (meth)acrylate polymer as the filler (b), and the polymerization initiator may remain in the non-crosslinkable (meth)acrylate polymer produced. Therefore, when a non-crosslinkable (meth)acrylate polymer in which the polymerization initiator remains is used for the resin artificial tooth of the present invention, it can be used instead of or as part of the polymerization initiator (c) without any problem.

The content of the polymerization initiator (c) for use in the curable dental composition of the present invention can be appropriately selected depending on the application, and the method for producing a block as the resin material for dental cutting and machining, and is preferably in the range from 0.01 to 10 parts by weight, more preferably in the range from 0.1 to 5 parts by weight, further preferably in the range from 0.1 to 2 parts by weight based on 100 parts by weight of the polymerizable monomer (a). If the amount of the polymerization initiator (c) to be compounded is less than 0.01 parts by weight, polymerization does not sufficiently progress to deteriorate mechanical strength, and if the amount is more than 10 parts by weight, the polymerization initiator (c) may be precipitated from the composition. When the polymerizable monomer (a) is the monofunctional polymerizable monomer having a boiling point of 50 to 200° C. and the filler (b) is the non-crosslinkable (meth)acrylate polymer, a content of the polymerization initiator of 0.1 parts by weight or more allows polymerization and curing to be uniform, and can inhibit sufficient physical properties from not being achieved due to the presence of the remaining unreacted monomer, polymerization defect, or the like. If the content is 5 parts by weight or less, the following problem is suppressed: polymerization and curing progress quickly not to enable to control the rate of polymerization of the monofunctional polymerizable monomer and not to take a margin for operation in production of a disc, resulting in rapid curing.

When the polymerization initiator (c) is used in the composite resin layer forming the composite resin artificial tooth, it can be used without particular limitation as long as the content thereof is in the range from 0.01 to 10 parts by weight, preferably in the range from 0.05 to 5 parts by weight, more preferably in the range from 0.1 to 5 parts by weight based on 100 parts by weight of the polymerizable monomer (a). If the amount of the polymerization initiator (c) to be compounded is less than 0.01 parts by weight, polymerization does not sufficiently progress to deteriorate mechanical properties, and if the amount is more than 10 parts by weight, polymerization and curing rapidly occur and therefore defects such as local shrinkage, cracking, clouding and chips can be caused.

Furthermore, when the polymerization initiator (c) is used for the resin artificial tooth in which the polymerizable monomer (a) is the monofunctional polymerizable monomer having a boiling point of 50 to 200° C. and the filler (b) is the non-crosslinkable (meth)acrylate polymer, the content thereof is preferably in the range from 0.1 to 5 parts by weight, more preferably in the range from 0.1 to 2 parts by weight based on 100 parts by weight of the polymerizable monomer (a). If the content of the polymerization initiator is less than 0.1 parts by weight, polymerization and curing do not occur uniformly, and sufficient physical properties are not achieved due to the presence of the remaining unreacted monomer, polymerization defect, or the like. If the content is more than 5 parts by weight, the following problem is caused: polymerization and curing progress too quickly to enable to control the rate of polymerization of the monofunctional polymerizable monomer for uniform molding, thereby deteriorating physical properties to result in rapid curing.

For the chain transfer agent (d) for use in the curable dental composition of the present invention, a known compound can be used without any limitation. Specific examples include mercaptan compounds such as n-butylmercaptan and n-octylmercaptan, terpenoid compounds such as limonene, myrcene, α-terpinene, β-terpinene, γ-terpinene, terpinolene, β-pinene and α-pinene, and an α-methylstyrene dimer. Among these chain transfer materials, terpenoid compounds are particularly preferable. Specifically, α-terpinene, β-terpinene and γ-terpinene are particularly preferable. These chain transfer agents can be used not only singly but also in combinations of two or more. In particular, γ-terpinene is most preferable. The amount of such a chain transfer agent to be added is preferably 0.001 to 1 part by weight, particularly preferably 0.1 parts by weight or more and 0.5 parts by weight or less based on 100 parts by weight of the polymerizable monomer (a). If the amount of the chain transfer agent (d) to be compounded is less than 0.001 parts by weight, strain of the inside, caused in polymerization of the dental curable composition, cannot be sufficiently suppressed. If the amount is more than 1 part by weight, the amount of the unreacted polymerizable monomer remaining in the composition after curing may be increased to deteriorate mechanical strength.

When the polymerizable monomer (a) is the monofunctional polymerizable monomer having a boiling point of 50 to 200° C. and the filler (b) is the non-crosslinkable (meth)acrylate polymer, the amount of the chain transfer agent to be added is preferably 0.001 to 1 part by weight, particularly preferably 0.1 to 0.5 parts by weight based on 100 parts by weight of the polymerizable monomer (a). If the content of the chain transfer agent is less than 0.001 parts by weight, the rate of polymerization and curing cannot be decreased, strain is generated in molding, and defects such as local shrinkage, cracking, clouding and chips, and incorporation of gas bubbles due to foaming cannot be suppressed. On the other hand, if the content is 1 part by weight or more, polymerization and curing do not progress and sufficient physical properties cannot be achieved.

When the chain transfer agent (d) is used in the composite resin layer forming the composite resin artificial tooth of the present invention, the content thereof is preferably in the range from 0.001 to 1 part by weight, more preferably in the range from 0.1 to 0.5 parts by weight based on 100 parts by weight of the polymerizable monomer (a). If the content of the chain transfer agent (d) is less than 0.001 parts by weight, rapid polymerization and curing can occur in molding with heating and pressure to cause defects such as local shrinkage, cracking, clouding and chips to be generated. On the other hand, if the content is more than 1 part by weight, the polymerization and curing reaction may be suppressed to thereby cause the proportion of the unreacted polymerizable monomer present to be higher, resulting in deterioration in material properties.

When the chain transfer agent is used in the resin artificial tooth in which the polymerizable monomer (a) is the monofunctional polymerizable monomer having a boiling point of 50 to 200° C. and the filler (b) is the non-crosslinkable (meth)acrylate polymer, the content thereof is in the range from 0.001 to 1 part by weight, preferably 0.001 to 3 parts by weight, particularly preferably 0.1 to 0.5 parts by weight based on 100 parts by weight of the polymerizable monomer (a). If the content of the chain transfer agent is less than 0.001 parts by weight, the rate of polymerization and curing cannot be decreased, strain is generated in molding, and defects such as local shrinkage, cracking, clouding and chips, and incorporation of gas bubbles due to foaming cannot be suppressed. On the other hand, if the content is 3 parts by weight or more, polymerization and curing do not progress and sufficient physical properties cannot be achieved.

To the dental curable composition of the present invention, a component such as an excipient typified by fumed silica, an ultraviolet absorber such as 2-hydroxy-4-methylbenzophenone, a polymerization inhibitor such as hydroquinone, hydroquinone monomethyl ether or 2,5-ditert-butyl-4-methylphenol, a discoloration inhibitor, an antibacterial material, a coloring pigment, or other conventionally known additive can be if necessary added arbitrarily, in addition to the above components (a) to (d).

In the composite resin artificial tooth of the present invention, at least one layer including a base layer that can chemically adhere to a denture base is an acrylic resin layer. For (e) a monofunctional (meth)acrylate polymerizable monomer that can be used in the acrylic resin layer forming the composite resin artificial tooth of the present invention, any monomer among known monofunctional (meth)acrylate polymerizable monomers having an acryloyl group and/or a methacryloyl group, commonly used in the field of dentistry, can be used without any limitation. In the present invention, the term "monofunctional (meth)acrylate polymerizable monomer" inclusively refers to both of an acryloyl group-containing polymerizable monomer and a methacryloyl group-containing polymerizable monomer.

Specific examples of the monofunctional (meth)acrylate polymerizable monomer (e) include the following. Examples of the monofunctional (meth)acrylate polymerizable monomer include (meth)acrylates such as methyl (meth)acrylate, ethyl (meth)acrylate, butyl (meth)acrylate, hexyl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, glycerol (meth)acrylate and isobornyl (meth)acrylate, silane compounds such as γ-(meth)acryloyloxypropyl trimethoxysilane and γ-(meth)acryloyloxypropyl triethoxysilane, and nitrogen-containing compounds such as 2-(N,N-dimethylamino) ethyl (meth)acrylate and N-methylol (meth)acrylamide. These monofunctional (meth)acrylate polymerizable monomers can be used not only singly but also in combinations of a plurality thereof.

The content of the monofunctional (meth)acrylate polymerizable monomer (e) that can be used in the acrylic resin layer forming the composite resin artificial tooth of the present invention is not particularly limited, and in particular preferably in the range from 10 to 70 parts by weight, more preferably in the range from 10 to 50 parts by weight, further preferably in the range from 20 to 40 parts by weight. If the content of the monofunctional (meth)acrylate polymerizable monomer is less than 10 parts by weight, adhesiveness to a denture base is deteriorated, and on the other hand, if the content is more than 70 parts by weight, the following problem is caused: polymerization shrinkage of a resin component is increased to thereby deteriorate moldability, making it impossible to achieve stable dimensional stability, for example.

(f) A non-crosslinkable (meth)acrylate polymer that can be used in the acrylic resin layer forming the composite resin artificial tooth of the present invention is not particularly limited as long as it is swollen by a monofunctional (meth) acrylate polymerizable monomer, and a polymer obtained by homopolymerizing the (meth)acrylate polymerizable monomer, a polymer obtained by copolymerizing a plurality of such (meth)acrylate polymerizable monomers, a polymer obtained by copolymerizing the (meth)acrylate polymerizable monomer with another monofunctional polymerizable monomer, or the like can be used without any limitation. Specific examples of the (meth)acrylate polymer include homopolymers such as polymethyl (meth)acrylate, polyethyl (meth)acrylate, polypropyl (meth)acrylate, polyisopropyl (meth)acrylate, polyisobutyl (meth)acrylate and polybutyl (meth)acrylate, and copolymers of a combination of two or more among methyl (meth)acrylate, ethyl (meth) acrylate, propyl (meth)acrylate, isopropyl (meth)acrylate, isobutyl (meth)acrylate and butyl (meth)acrylate, but are not limited thereto. These non-crosslinkable (meth)acrylate polymers can be used not only singly but also in combinations of a plurality thereof. Among these non-crosslinkable (meth)acrylate polymers, polymethyl methacrylate, polyethyl methacrylate, or a copolymer of methyl methacrylate with ethyl methacrylate is preferably used.

Such a non-crosslinkable (meth)acrylate polymer is not limited at all in terms of the polymerization method, and can be produced by any polymerization method such as emulsion polymerization or suspension polymerization without any problem. The non-crosslinkable (meth)acrylate polymer can be used without any limitation, even if having any shape such as a spherical shape, a crushed shape or a hollow shape, but preferably a spherical shape.

The non-crosslinkable (meth)acrylate polymer can be used without any limitation as long as the average particle size (50 parts) thereof is in the range from 1 to 300 μm, preferably in the range from 1 to 200 μm, further preferably in the range from 5 to 150 μm. The non-crosslinkable (meth)acrylate polymer can be used without any limitation as long as the weight average molecular weight thereof is in the range from 10000 to 2000000, preferably in the range from 50000 to 1500000, further preferably in the range from 100000 to 1500000.

In addition, any one can be used without any limitation, in which the surface of an organic filler, an inorganic filler, an organic/inorganic composite type filler, an organic/inorganic compound, an organic/inorganic pigment or the like is subjected to secondary processing such as a surface modification treatment or a composite-forming treatment in which the surface is covered with the non-crosslinkable (meth)acrylate polymer.

The non-crosslinkable (meth)acrylate polymer (f) that can be used in the acrylic resin layer forming the composite resin artificial tooth of the present invention can be used without any limitation as long as the content thereof is in the range from 30 to 90 parts by weight, preferably in the range from 50 to 90 parts by weight, further preferably in the range from 60 to 80 parts by weight.

If the content of the non-crosslinkable (meth)acrylate polymer is less than 30 parts by weight, adhesiveness to a denture base is deteriorated, and on the other hand, if the content is more than 90 parts by weight, the following problem is caused: polymerization shrinkage of a resin component is increased to thereby deteriorate moldability, making it impossible to achieve stable dimensional stability, for example.

To the composite resin layer or the acrylic resin layer forming the composite resin artificial tooth of the present invention, a component such as an excipient typified by fumed silica, an ultraviolet absorber such as 2-hydroxy-4-methylbenzophenone, a polymerization inhibitor such as hydroquinone, hydroquinone monomethyl ether or 2,5-di-tert-butyl-4-methylphenol, a discoloration inhibitor, an antibacterial material, a coloring pigment, or other conventionally known additive can be if necessary added arbitrarily, in addition to the above components (a) to (d).

The method for producing a resin for dental cutting and machining, using the dental curable composition of the present invention, is not limited at all. Examples include a method of packing in a mold the dental curable composition, to which the heat polymerization initiator is added, for production with pressure and heating, and a method of packing in a mold the dental curable composition, to which the photo-polymerization initiator and the heat polymerization initiator are added, and subjecting a surface layer portion to polymerization by irradiation with light, before heating, for sufficient curing to the inside.

The size and the shape of the resin material for dental cutting and machining, produced using the dental curable composition of the present invention, are not limited at all. Examples include a prism shape of 12×14×18 mm, and a disc shape having 10 to 30 mm in thickness×98 mm in diameter.

The method for producing the composite resin artificial tooth of the present invention is not limited at all. Examples include a compression molding method of packing in a mold a rice cake-like raw material, in which a paste or powder material is admixed with a liquid material, for pressurizing and heating, and an injection molding method of injecting the raw material into a mold at a constant pressure, but are not limited thereto. In particular, a production method of sequentially subjecting each of the composite resin layer or the acrylic resin layer singly to polymerization and curing with heating and pressure, for stacking is preferable.

When the composite resin artificial tooth of the present invention has a monolayer or multilayer structure having the composite resin layer, chemical adhesion with a denture base cannot be expected, and therefore an adhesive primer is used or a maintaining hole is formed for providing mechanical fitting without any limitation. When the composite resin artificial tooth of the present invention is configured from at least one layer as the composite resin layer and at least one layer as the acrylic resin layer, including a base layer that can chemically adhere to a denture base, it can have a multilayer structure without any limitation in the number of layers and the types thereof. The shape and the size thereof are not limited, and various shapes and sizes can be adopted without any problem.

Examples

[Dental Curable Composition]

Hereinafter, Examples of the dental curable composition of the present invention including (a) a polymerizable monomer and (b) a filler in a weight ratio of 10:90 to 70:30, and including 0.01 to 10 parts by weight of (c) a polymerization initiator and 0.001 to 1 part by weight of (d) a chain transfer agent being a terpenoid compound based on 100 parts by weight of the polymerizable monomer (a) are specifically described, but the present invention is not intended to be limited to these Examples. Test methods for evaluating performances of the dental curable composition prepared in each of Examples and Comparative Examples are as follows.

(1) Crack Confirmation Test

Objective: Evaluation of strain in production of large-sized block cured body

Method: an aluminum alloy mold was filled with a curable composition, sandwiched between nylon films at the top and bottom, and subjected to pressure-welding by an aluminum alloy flat panel. Thereafter, hot press was conducted using a hot press machine (manufactured by Shofu Inc.) under conditions of a press pressure of 2 t, a press plate temperature of 100° C. and a press time of 30 minutes to provide a block cured body of φ100×14 mm. The operation was repeatedly conducted five times to produce five block cured bodies. Each of the block cured bodies was visually observed, and a case where even one crack was generated was defined as "Present" and a case where no cracks were observed was defined as "Absent."

(2) Bending Strength Test

Objective: Evaluation of bending strength of test specimen cut out from block cured body Method: an aluminum alloy mold was filled with a dental curable composition, sandwiched between nylon films at the top and bottom, and subjected to pressure-welding by an aluminum alloy flat panel. Thereafter, hot press was conducted using a hot press machine (manufactured by Shofu Inc.) under conditions of a press pressure of 2 t, a press plate temperature of 95° C. and a press time of 10 minutes, to provide a block cured body of 12×14×18 mm. The block cured body was cut using a precision cutting machine to test pieces of 18×2×2 mm, and thereafter the surfaces of the test pieces were buffed to thereby provide test specimens (five specimens were produced). The test was performed using a universal tester at a distance between supporting points of 10 mm and a crosshead speed of 1.0 mm/min, for evaluation by the average of the results of the five test specimens.

(3) Weight-Drop Test

Objective: Evaluation of impact resistance of test specimen cut out from block cured body Method: a block cured body of 12×14×18 mm was produced in the same manner as in the bending strength test. The block cured body was cut using a precision cutting machine to test pieces of 12×14×2 mm, and thereafter the surfaces of the test pieces were buffed to thereby provide test specimens (ten specimens were produced). Each of the test specimens was placed on a stainless-steel stage and a stainless-steel spherical body having a weight of 110 g was freely dropped from a height of 3 cm. When no change was observed with respect to each of the test specimens, the drop height was increased by 1 cm, and a drop distance at which cleavage or breaking occurred in each of the test specimens was defined as the distance at breaking, and evaluated by the average of the results of the ten test specimens.

Compounds used in Examples of the present invention and abbreviations thereof are shown below.
UDMA: urethane dimethacrylate
Bis-GMA: 2,2-bis(4-(3-(meth)acryloyloxy-2-hydroxy-propoxy)phenyl)propane
TEGDMA: triethylene glycol dimethacrylate
BPO: benzoyl peroxide R-972: Aerosil R-972 (manufactured by Nippon Aerosil Co., Ltd.)
γ-MPS: γ-methacryloxypropyl trimethoxysilane The catalogue values of the average particle size, the pore volume and the BET specific surface area of each silica filler are shown in Table 1. Silica fillers (1) and (2) were each appropriately subjected to a silane treatment and used for preparation of a dental composition.

TABLE 1

|  | Average particle size (μm) | Pore volume (mL/g) | BET specific surface area (m²/g) |
|---|---|---|---|
| Silica filler (1) | 0.9 | — | 4 |
| Silica filler (2) | 5-7 | 0.3 | 150 |

Each of resin compositions (I1 to I9) was prepared at each composition shown in Table 2.

TABLE 2

| Resin composition No. | Amount to be compounded (g) | | | | | | |
|---|---|---|---|---|---|---|---|
| | (a) Polymerizable monomer | | | (c) Polymerization initiator | (d) Chain transfer agent | | |
| | UDMA | Bis-GMA | TEGDMA | BPO | α-Terpinene | β-Terpinene | γ-Terpinene |
| I1 | 70 |  | 30 | 0.3 | 0.5 |  |  |
| I2 |  | 70 | 30 | 0.3 | 0.5 |  |  |
| I3 | 70 |  | 30 | 0.3 |  | 0.5 |  |
| I4 | 70 |  | 30 | 0.3 |  |  | 0.5 |
| I5 | 70 |  | 30 | 0.3 |  |  | 0.1 |
| I6 | 70 |  | 30 | 0.3 |  |  | 0.3 |
| I7 | 70 |  | 30 | 0.3 |  |  | 1 |
| I8 | 70 |  | 30 | 0.3 |  |  |  |
| I9 |  | 70 | 30 | 0.3 |  |  |  |

Each of the resin compositions recited in Table 2 was used to prepare each of curable compositions (Examples 1 to 7 and Comparative Examples 1 and 2) according to each composition in Table 3. Each of the curable compositions was used to produce each block cured body, and the crack confirmation test was performed. The results are shown in Table 3.

TABLE 3

| | (b)Filler | | | Resin composition | | | | | | Presence of cracks |
|---|---|---|---|---|---|---|---|---|---|---|
| | Silica filler (1) treated with silane | Silica filler (2) treated with silane | R-972 | I1 | I2 | I3 | I4 | I8 | I9 | |
| Example 1 | 30 |  | 2 | 68 |  |  |  |  |  | Absent |
| Example 2 | 70 |  | 2 | 28 |  |  |  |  |  | Absent |
| Example 3 | 85 |  | 2 | 13 |  |  |  |  |  | Absent |
| Example 4 |  | 70 | 2 | 28 |  |  |  |  |  | Absent |
| Example 5 | 70 |  | 2 |  | 28 |  |  |  |  | Absent |
| Example 6 | 70 |  | 2 |  |  | 28 |  |  |  | Absent |
| Example 7 | 70 |  | 2 |  |  |  | 28 |  |  | Absent |
| Comparative Example 1 | 70 |  | 2 |  |  |  |  | 28 |  | Present |
| Comparative Example 2 | 70 |  | 2 |  |  |  |  |  | 28 | Present |

Examples 1 to 3 were each a system in which resin composition I1, to which α-terpinene was added as the chain transfer agent, was used and the amount of the filler (b) to be added was changed. A block cured body of φ100×14 mm could be produced without any cracks generated, even by a dental curable composition in which the amount of the filler to be added was increased.

Example 4 was a system in which resin composition I1, to which α-terpinene was added as the chain transfer agent, was used and the type of the filler (b) was changed. A block cured body of φ100×14 mm could be produced without any cracks generated, even when the type of the filler was changed.

Example 5 was a system in which while α-terpinene was added as the chain transfer agent, resin composition I2, in which a portion of the polymerizable monomer was changed as compared with resin composition I1, was used. A block cured body of φ100×14 mm could be produced without any cracks generated, even when the type of the polymerizable monomer (a) was changed.

Examples 6 and 7 were each a system in which each of resin compositions I3 and I4, in which the type of the chain transfer agent was β-terpinene and γ-terpinene, respectively, was used. A block cured body of φ100×14 mm could be produced without any cracks generated, even when the type of the chain transfer agent was changed.

Comparative Examples 1 and 2 were each a system in which each of resin compositions I8 and I9, in which no chain transfer agent was added into the resin composition, was used. Cracking was generated due to no chain transfer agent included in each of the curable compositions in production of each block cured body.

Next, each of the resin compositions recited in Table 2 was used to prepare each of curable compositions (Examples 8 to 11 and Comparative Example 3) according to each composition in Table 4. Each of the curable composition was used to produce each block cured body, and thereafter the bending strength test and the weight-drop test were performed. The results are shown in Table 4.

TABLE 4

| | (b) Filler | | | | | | | Bending | Distance at |
| | Silica filler (2) treated | | Resin composition | | | | | strength | breaking |
| | with silane | R-972 | I5 | I6 | I4 | I7 | I8 | (MPa) | (cm) |
| Example 8 | 70 | 2 | 28 | | | | | 198 | 14.5 |
| Example 9 | 70 | 2 | | 28 | | | | 192 | 15.9 |
| Example 10 | 70 | 2 | | | 28 | | | 199 | 17.6 |
| Example 11 | 70 | 2 | | | | 28 | | 161 | 15.4 |
| Comparative Example 3 | 70 | 2 | | | | | 28 | 196 | 13.3 |

Examples 8 to 11 were each a system in which the curable composition prepared by the resin composition, in which the amount of the chain transfer agent to be added was changed, was used. An increase in the amount of the chain transfer agent to be added increased the distance at breaking by the weight-drop test of the block cured body produced, to enhance the impact resistance. In Examples 11, the curable composition prepared by the resin composition, in which the amount of the chain transfer agent to be added was larger than those in Examples 8 to 10, was used and therefore the bending strength was slightly deteriorated and the distance at breaking was also shortened.

In Comparative Example 3, the curable composition including no chain transfer agent in the resin composition was used, and therefore cracks were generated in production of the block cured body and the distance at breaking by the weight-drop test was also shorter than those in Examples 8 to 11.

Next, Examples of the dental curable composition of the present invention, in which
the polymerizable monomer (a) was a monofunctional polymerizable monomer having a boiling point of 50 to 200° C., and
the filler (b) was a non-crosslinkable (meth)acrylate polymer are specifically described, but the present invention is not intended to be limited to these Examples. Test methods for evaluating performances of the dental curable composition prepared in each of Examples, Reference Examples and Comparative Examples are as follows.

Compounds used in Examples of the present invention and abbreviations thereof are shown below.
(a: monofunctional polymerizable monomer having a boiling point of 50 to 200° C.)
MMA: methyl methacrylate, boiling point: 101° C.
NEMA: n-butyl (meth)acrylate, boiling point: 162° C.
(b: non-crosslinkable (meth)acrylate polymer)
PMMA (1): polymethyl methacrylate powder, D50 average particle size: 50 μm; weight average molecular weight: 800000
PMMA (2): polymethyl methacrylate powder, D50 average particle size: 100 μm; weight average molecular weight: 800000
PEMA: polyethyl methacrylate powder, D50 average particle size: 50 μm; weight average molecular weight: 800000
PMMA (3): polymethyl methacrylate powder, D50 average particle size: 500 μm; weight average molecular weight: 2000000
(c: polymerization initiator)
BPO: benzoyl peroxide
(d: chain transfer agent)
α-terpinene
β-terpinene
γ-terpinene
limonene
(e) polymerizable monomer other than (a)
EMA: ethylene dimethacrylate, boiling point: 260° C.

The test method and the evaluation method of each test are shown below.

(1) Confirmation Tests of Cracks and Foaming, and Local Shrinkage

Objective: Evaluation of cracks and foaming, and deformation in production of large-sized molded product using dental curable composition Method: an aluminum alloy mold was filled with a dental curable composition in which a powder material and a liquid material were admixed (admixing ratio: monomer prepared/polymer=40/60), and sandwiched between nylon films at the top and bottom and subjected to pressure-welding by an aluminum alloy flat panel. Thereafter, hot press was conducted using a hot press machine (manufactured by Shofu Inc.) under conditions of a press pressure of 2 t, a press plate temperature of 80° C. and a press time of 30 minutes to provide a cured body of φ100×20 mm. The operation was repeatedly conducted five times to produce five cured bodies. Each of the cured bodies was visually observed, and the degrees of cracks or inner foaming, and deformation were rated on a 4-point scale: ⊙: very good; ○: slightly good; Δ: slightly problematic, but not problematic clinically; and ×: problematic and incapable of being used clinically.

(2) Bending Strength

A molded body was cut to a size of 4 mm×4 mm×14 mm, a load was applied to the center portion thereof using a universal tester at a crosshead speed of 1 mm/min to measure the load at fracture, measuring the three-point bending strength. The number of samples was six, and the average of the results thereof was determined. The bending strength was clinically preferably 80 MPa or more, further preferably 100 MPa or more.

The method for producing a resin material for dental cutting and machining was as follow: (a), (c), (e), and (d) were mixed at a compounding ratio recited in Table 1 to provide a liquid component, and (b) and (f) were mixed to provide a powder component; the liquid component and the powder component were mixed so that the compounding ratio recited in Table 1 was obtained, and an artificial tooth-shaped mold was filled with the resulting mixture and heated at 100° C. for 1 minute; and the resultant was left to be cooled to provide a resin material for dental cutting and machining.

TABLE 5

| | Composition | Example 12 | Example 13 | Example 14 | Example 15 | Example 16 | Example 17 | Example 18 | Example 19 |
|---|---|---|---|---|---|---|---|---|---|
| (a) | MMA | 100 | 100 | 100 | 100 | 100 | 100 | 100 | 100 |
| (e) | EMA | | | | | | | | |
| (b) | PMMA(1) | 200 | | 100 | 190 | | | | |
| | PMMA(2) | | 200 | 100 | | 200 | 200 | 200 | 200 |
| (f) | FASG | | | | 10 | | | | |
| (c) (Outer percentage) | BPO | 0.2 | 0.2 | 0.2 | 0.2 | 0.2 | 0.2 | 0.2 | 0.2 |
| (d) (Outer percentage) | α-Terpinene | 0.5 | 0.5 | 0.5 | 0.5 | | | | |
| | β-Terpinene | | | | | | 0.5 | | |
| | γ-Terpinene | | | | | | | 0.1 | 0.3 | 0.5 |
| | Total | 300.7 | 300.7 | 300.7 | 300.7 | 300.7 | 300.3 | 300.5 | 300.7 |
| Test items | Cracks | ⊙ | ⊙ | ⊙ | ⊙ | ⊙ | ⊙ | ○ | ⊙ |
| | Foaming | ○ | ⊙ | ○ | ○ | ⊙ | ⊙ | ⊙ | ⊙ |
| | Local shrinkage | ○ | ○ | ○ | ○ | ⊙ | ○ | ⊙ | ⊙ |
| | Bending strength [Mpa] | 121 | 126 | 131 | 110 | 140 | 141 | 125 | 132 |

| | Composition | Example 20 | Example 21 | Example 22 | Example 23 | Example 24 | Example 25 | Comparative Example 4 |
|---|---|---|---|---|---|---|---|---|
| (a) | MMA | 100 | 100 | 100 | 100 | 100 | | 100 |
| (e) | EMA | | 10 | 20 | 20 | 20 | 100 | |
| (b) | PMMA(1) | | | | 100 | | | |
| | PMMA(2) | 200 | 200 | 200 | | 300 | 200 | 200 |
| (f) | FASG | | | | | | | |
| (c) (Outer percentage) | BPO | 0.2 | 0.2 | 0.2 | 0.2 | 0.2 | 0.2 | 0.2 |
| (d) (Outer percentage) | α-Terpinene | | | | | | | |
| | β-Terpinene | | | | | | | |
| | γ-Terpinene | 3 | 1 | 0.5 | 0.5 | 0.5 | 0.5 | |
| | Total | 303.2 | 311 | 320.7 | 220.7 | 420.7 | 300.7 | 300.2 |
| Test items | Cracks | ⊙ | ○ | ○ | ⊙ | ⊙ | X | ○ |
| | Foaming | ⊙ | ⊙ | ⊙ | ⊙ | ○ | ⊙ | X |
| | Local shrinkage | ⊙ | ○ | ⊙ | ⊙ | ⊙ | X | Δ |
| | Bending strength [Mpa] | 85 | 113 | 118 | 116 | 121 | 141 | 134 |

(parts by weight)

From the above results, the resin material in Comparative Example 4, when not including Component (d), cannot be clinically used because of being large in foaming; and the resin material in Example 25, in which the boiling point of Component (a) is high, can withstand use, but is larger in cracks and local shrinkage.

[Composite Resin Artificial Tooth]

Next, Examples of the composite resin artificial tooth of the present invention which is a composite resin artificial tooth having a monolayer or multilayer structure, in which a composite resin layer thereof includes (a) a polymerizable monomer,
(b) a filler,
(c) a polymerization initiator, and
(d) a chain transfer agent, as well as the composite resin artificial tooth of the present invention, which is configured from at least one layer configured from a composite resin layer including (a) a polymerizable monomer,
(b) a filler,
(c) a polymerization initiator, and
(d) a chain transfer agent, and at least one layer including a base layer that can chemically adhere to a denture base, configured from an acrylic resin layer including (e) a monofunctional (meth)acrylate polymerizable monomer,
(f) a non-crosslinkable (meth)acrylate polymer,
(c) a polymerization initiator, and
(d) a chain transfer agent are specifically described, but the present invention is not intended to be limited to these Examples. Test methods for evaluating performances of the composite resin artificial tooth prepared in each of Examples and Comparative Examples are as follows.

(1) Bending Test

Objective of evaluation: To evaluate bending strength of a test specimen obtained by molding a composite resin composition.

Evaluation Method:

After a stainless-steel mold (25×2×2 mm: cuboid type) was filled with the composite resin composition prepared, molding with pressure and heating was conducted under conditions of a mold press pressure of 3 t, a molding temperature (base layer) of 100° C. and a molding temperature (enamel layer) of 120° C., and a press time of 10 minutes. Thereafter, a molded product was taken out from the mold, and then immersed in water at 37° C. for 24 hours to provide a test specimen.

In the bending test, an Instron universal tester (Instron 5567 manufactured by Instron) was used to measure the bending strength at a distance between supporting points of 20 mm and a crosshead speed of 1 mm/min.

(2) Non-Defective Molded Product Test

Objective of Evaluation:

To evaluate molding properties of a molded product having a bilayer structure (acrylic resin composition and composite resin composition) formed using a simulated artificial tooth mold (bilayer structure in which a base acrylic resin layer and a composite resin layer each having a thickness differing in a transitive manner were stacked: FIG. 1).

Evaluation Method:

The acrylic resin composition was packed in the base layer differing in thickness in a transitive manner located on the lower portion of the simulated artificial tooth mold (10 mm×10 mm×5 mm) illustrated in FIG. 1, and thereafter molding with pressure and heating was conducted. Thereafter, the composite resin composition was packed in the composite resin layer differing in thickness in a transitive manner located on the upper portion of the acrylic resin layer cured, and thereafter molding with pressure and heating was conducted. One hundred of the molded bodies were produced, and cracking, chips, and the like generated in the simulated artificial tooth were confirmed to thereby evaluate molding properties. Herein, the molding with pressure and heating was conducted under conditions of a mold press pressure of 3 t, a molding temperature (base layer) of 100° C. and a molding temperature (composite resin layer) of 120° C., and a press time of 10 minutes. As a result, a molded product without any defects such as cracking and chips at all was defined as a non-defective product, and the non-defective rate was calculated. A non-defective rate of 90 parts or more is defined to fall within the relevant range.

(3) Interface Adhesion State Confirmation Test

Objective of Evaluation:

To evaluate the influence on the interface (adhesion surface of base layer and composite resin layer) in application of a forced pressure load to a molded product having a bilayer structure (acrylic resin composition and composite resin composition) formed using a simulated artificial tooth mold (bilayer structure in which a base acrylic resin layer and a composite resin layer each having a thickness differing in a transitive manner were stacked: FIG. 1).

Figure 2:
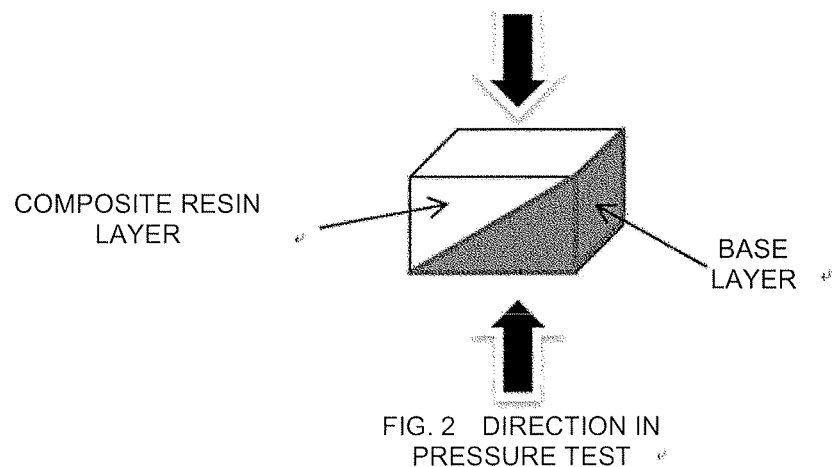
FIG. 2 is a view indicating the direction in the pressure test in an interface adhesion state confirmation test.

Evaluation Method:

Ten were randomly taken out from 100 of the simulated artificial teeth determined as a non-defective product by the non-defective molded product test, and were used as test specimens. The compression resistance (pressure test) of each of the test specimens was measured using an Instron universal tester (Instron 5567 manufactured by Instron). The pressure direction of each of the test specimens is indicated in FIG. 2. A measurement condition was as follows: crosshead speed: 1 mm/min; and the influence on the interface at a displacement of 0.5 mm was observed and evaluated.

The rating criteria were as follow: ○: not changed; Δ: partially clouded; and x: clouded at the entire interface or separated at the interface.

Compounds used in Examples of the present invention and abbreviations thereof are shown below.

(a) polymerizable monomer

UDMA: urethane dimethacrylate

Bis-GMA: 2,2-bis(4-(3-(meth)acryloyloxy-2-hydroxypropoxy)phenyl) propane

TEGDMA: triethylene glycol dimethacrylate (b) filler silica: average particle size: 0.9 μm; BET specific surface area: 4.0 m²/g, treated with silane by 7-methacryloxypropyl trimethoxysilane and used for preparing composition.

(c) polymerization initiator

BPO: benzoyl peroxide (e) monofunctional (meth)acrylate polymerizable monomer

MMA: methyl methacrylate (f) non-crosslinkable (meth)acrylate polymer

PMMA: polymethyl methacrylate, 50-part average particle size: 50 μm (d) chain transfer agent α-terpinene β-terpinene γ-terpinene Each of acrylic resin compositions (B1 to B9 and BC1) was prepared according to each composition shown in Table 6.

TABLE 6

| | | Amount to be compounded (parts by weight) | | | | |
|---|---|---|---|---|---|---|
| | | | Liquid material | | | |
| Acrylic resin composition No. | Powder material (f) Non-crosslinkable (meth)acrylate polymer PMMA | (e) Monofunctional (meth)acrylate polymerizable monomer MMA | (c) Polymerization initiator BPO | (d) Chain transfer agent | | |
| | | | | α-Terpinene | β-Terpinene | γ-Terpinene |
| B1 | 65.0 | 35.0 | 0.04 (0.11) | | | 0.04 (0.11) |
| B2 | 65.0 | 35.0 | 0.30 (0.10) | 0.04 (0.11) | | |
| B3 | 65.0 | 35.0 | 0.30 (0.10) | | 0.04 (0.11) | |

TABLE 6-continued

| | Amount to be compounded (parts by weight) | | | | | |
|---|---|---|---|---|---|---|
| | Powder material (f) | Liquid material | | | | |
| Acrylic resin composition No. | Non-crosslinkable (meth)acrylate polymer PMMA | (e) Monofunctional (meth)acrylate polymerizable monomer MMA | (c) Polymerization initiator BPO | (d) Chain transfer agent | | |
| | | | | α-Terpinene | β-Terpinene | γ-Terpinene |
| B4 | 65.0 | 35.0 | 0.30 (0.10) | | | 0.04 (0.11) |
| B5 | 65.0 | 35.0 | 0.50 (0.14) | | | 0.04 (0.11) |
| B6 | 65.0 | 35.0 | 1.50 (4.30) | | | 0.04 (0.11) |
| B7 | 65.0 | 35.0 | 0.30 (0.10) | | | 0.03 (0.09) |
| B8 | 65.0 | 35.0 | 0.30 (0.10) | | | 0.15 (0.43) |
| B9 | 65.0 | 35.0 | 0.30 (0.10) | | | 0.40 (1.14) |
| BC1 | 65.0 | 35.0 | 0.50 (0.14) | | | |

(Note)
Admixing ratio of powder material/liquid material: 65/35 (weight ratio).
(Note)
In Table, values in brackets are part(s) by weight based on 100 parts by weight of monofunctional (meth)acrylate polymerizable monomer.

Each of composite resin compositions (E1 to E11 and EC1) was prepared according to each composition shown in Table 7.

TABLE 7

| | Amount to be compounded (parts by weight) | | | | | | | |
|---|---|---|---|---|---|---|---|---|
| Composite resin composition No. | (a) Polymerizable monomer | | | (b) Filler | (c) Polymerization initiator | (d) Chain transfer agent | | |
| | UDMA | Bis-GMA | TEGDMA | Silica filler | BPO | α-Terpinene | β-Terpinene | γ-Terpinene |
| E1 | 49 | | 21 | 30 | 0.21 (0.33) | | | 0.40 (0.44) |
| E2 | 42 | | 18 | 40 | 0.20 (0.33) | | | 0.20 (0.33) |
| E3 | 21 | | 9 | 70 | 0.10 (0.33) | | | 0.10 (0.33) |
| E4 | | 42 | 18 | 40 | 0.20 (0.33) | | | 0.20 (0.33) |
| E5 | 42 | | 18 | 40 | 0.40 (0.67) | | | 0.20 (0.33) |
| E6 | 42 | | 18 | 40 | 3.00 (5.00) | | | 0.20 (0.33) |
| E7 | 42 | | 18 | 40 | 0.30 (0.50) | 0.20 (0.33) | | |
| E8 | 42 | | 18 | 40 | 0.20 (0.33) | | 0.20 (0.33) | |
| E9 | 42 | | 18 | 40 | 0.20 (0.33) | | | 0.06 (0.10) |
| E10 | 42 | | 18 | 40 | 0.20 (0.33) | | | 0.60 (1.00) |
| E11 | 42 | | 18 | 40 | 0.20 (0.33) | | | 1.00 (1.67) |
| EC1 | 42 | | 18 | 40 | 0.20 (0.33) | | | |

(Note)
In Table, values in brackets are part(s) by weight based on 100 parts by weight of monofunctional (meth)acrylate polymerizable monomer.

Each of the composite resin compositions prepared was used to perform the bending test. The results are shown in Table 8.

TABLE 8

| | Composition No. | Bending strength (MPa) | Remarks |
|---|---|---|---|
| Composite resin composition | E1 | 112 | |
| | E2 | 136 | |
| | E3 | 156 | |
| | E4 | 149 | |
| | E5 | 151 | |
| | E6 | 148 | |
| | E7 | 133 | |
| | E8 | 132 | |
| | E9 | 140 | |
| | E10 | 145 | |
| | E11 | 129 | |
| | EC1 | — | Not tested due to incorporation of many gas bubbles and cracks |

Composite resin compositions E1 to E3 were each a system in which the amount of the filler being Component (b) to be compounded was changed. As the amount of the filler (b) was increased, the bending strength was higher.

Composite resin compositions E2 and E4 were each a system in which the type of the polymerizable monomer (a) (UDMA or Bis-GMA) was partially changed. While the same type of the chain transfer agent and the same amount thereof to be compounded were adopted, the difference in the type of the polymerizable monomer affected to cause a small difference in bending strength, but sufficient bending strength was exhibited.

Composite resin compositions E2, E5 and E6 were each a system in which the amount of the polymerization initiator (c) to be compounded was changed. The same type and the same amount of the chain transfer agent were adopted, and the bending strength was exhibited at the same level as one another without any influence.

Composite resin compositions E2, E7 and E8 were each a system in which while the amount of the chain transfer agent (d) to be compounded was the same as one another, the type (γ-terpinene, α-terpinene, β-terpinene) thereof was changed. The bending strength was exhibited at the same level as one another without any influence even by the change in the type of the chain transfer agent.

Composite resin compositions E2, E9, E10 and E11 were each a system in which the amount of the chain transfer agent (d) to be compounded was changed. When the amount of the chain transfer agent to be compounded was in the range from 0.06 (E9) to 0.6 (E10) parts by weight, the bending strength was exhibited at the same level as one another without any influence, but when the amount was 1.0 (E11) part by weight, the bending strength was found to be slightly deteriorated.

Composite resin composition EC1, without the chain transfer agent (d) compounded therein, caused many gas bubbles to be incorporated, and also caused cracks to be generated, and therefore a bending test specimen could not be produced therefrom.

Next, each of the composite resin compositions and the acrylic resin compositions prepared was used to perform the non-defective molded product test and the interface adhesion state confirmation test. The results are shown in Table 9.

TABLE 9

| | Composition No. | | Non-defective molded product test | | | Interface adhesion state confirmation test |
|---|---|---|---|---|---|---|
| | Acrylic resin composition | Composite resin composition | Non-defective rate (parts) | Main defective rate (parts) Cracks | Gas bubble | |
| Example 26 | B4 | E1 | 92 | 4 | 0 | ○ |
| Example 27 | B4 | E2 | 94 | 2 | 0 | ○ |
| Example 28 | B4 | E3 | 98 | 1 | 0 | ○ |
| Example 29 | B4 | E4 | 92 | 4 | 0 | ○ |
| Example 30 | B1 | E6 | 96 | 3 | 0 | ○ |
| Example 31 | B4 | E7 | 94 | 3 | 0 | ○ |
| Example 32 | B4 | E8 | 94 | 4 | 0 | ○ |
| Example 33 | B5 | E9 | 100 | 0 | 0 | ○ |
| Example 34 | B5 | E10 | 96 | 2 | 0 | ○ |
| Example 35 | B2 | E2 | 94 | 3 | 0 | ○ |
| Example 36 | B3 | E2 | 96 | 1 | 0 | ○ |
| Example 37 | B7 | E5 | 94 | 3 | 0 | ○ |
| Example 38 | B8 | E5 | 98 | 1 | 0 | ○ |
| Example 39 | B9 | E2 | 96 | 3 | 0 | ○ |
| Example 40 | B9 | E11 | 92 | 2 | 0 | ○ |
| Example 41 | B4 | E11 | 92 | 3 | 0 | ○ |
| Comparative Example 5 | B4 | EC1 | 16 | 45 | 74 | X |
| Comparative Example 6 | BC1 | EC1 | 8 | 55 | 81 | X |

As shown in Table 9, in each of Examples 26 to 41, the acrylic resin composition and the composite resin composition, to which the chain transfer agent was compounded, were used to form a simulated artificial tooth. As a result, while no generation of gas bubbles was observed at all, cracks were partially, but extremely slightly generated, and the non-defective rate was 90 parts or more in each case. In addition, the simulated artificial tooth as a non-defective product was used to perform the interface adhesion state confirmation test, and as a result, it was confirmed that there was no problem at the interface and the two compositions adhered firmly.

As shown in Table 9, in each of Comparative Example 5 and Comparative Example 6, the composite resin composition to which the chain transfer agent was not compounded was used to form a simulated artificial tooth. In each case, gas bubbles and cracks were generated too much to enable a simulated artificial tooth to be formed, and the non-defective rate was as very low as 16 parts in Comparative Example 5 and 8 parts in Comparative Example 6. Any specimens being a non-defective product were taken out therefrom and subjected to the interface adhesion state confirmation test, and as a result, it was confirmed that the entire interface on which the two compositions adhered was clouded or separated and dropped in all the specimens.

The chain transfer agent was compounded to the composition of the composite resin artificial tooth to thereby enable uniform polymerization and curing, deterioration in material properties due to compounding of the chain transfer agent was not observed, and shrinkage to be locally generated, cracking, clouding and chips were suppressed to achieve excellent physical properties.

Next, Examples of the resin artificial tooth of the present invention including
(a) a monofunctional polymerizable monomer having a boiling point of 50 to 200° C.,
(b) a non-crosslinkable (meth)acrylate polymer,
(c) a polymerization initiator, and
(d) a chain transfer agent
are described in detail, but the present invention is not intended to be limited to these Examples. Test methods for evaluating performances of the resin artificial tooth prepared in each of Examples, Reference Examples and Comparative Examples are as follows.

(1) Crack and Foaming Confirmation Test

Objective: Evaluation of cracks, inner foaming and local shrinkage of resin composition in molding Method: a liquid material composition and a powder material composition were admixed in the compounding ratio of each of Examples, the admixture was filled in an aluminum alloy mold (cavity portion: 10 mm×10 mm×10 mm), and thereafter a nylon film was interposed from above for pressure-welding by an aluminum alloy flat panel. Thereafter, hot press was conducted using a hot press machine (manufactured by Shofu Inc.) under conditions of a press pressure of 2 t, a press plate setting temperature of 100° C. and a press time of 10 minutes to provide a cured body of 10 mm×10 mm×10 mm.

The cured body was visually observed, and "cracks" or "inner foaming," and "local shrinkage" were rated at a 4-point scale (⊙: very good; ○: slightly good; Δ: slightly problematic, but not problematic clinically; and x: problematic and incapable of being used clinically), and any cured body rated as ⊙ to Δ was defined as a non-defective product. The non-defective rate is desirably 90 parts or more.

(2) Surface Hardness Test

Objective: Evaluation of surface hardness (physical property) of resin composition in molding Method: the surface hardness of the cured body formed in the crack and foaming confirmation test (1) above was measured using a Vickers hardness meter. The surface hardness was measured at five points and the average was calculated.

A hardness of 15 or more, preferably 18 or more, is defined to fall within the relevant range of the resin artificial tooth.

Compounds used in Examples of the present invention and abbreviations thereof are shown below.

(a) monofunctional polymerizable monomer having a boiling point of 50 to 200° C.
MMA (methyl methacrylate), boiling point: 101° C.
(b) non-crosslinkable (meth)acrylate polymer PMMA (1) (polymethyl methacrylate powder), average particle size (D50): 50 μm; weight average molecular weight: 800000
PMMA (2) (polymethyl methacrylate powder), average particle size (D50): 100 μm; weight average molecular weight: 800000
(c) polymerization initiator
BPO: benzoyl peroxide
(d) chain transfer agent
α-terpinene
β-terpinene
γ-terpinene
(e) polymerizable monomer other than (a)
EMA: ethylene glycol dimethacrylate, boiling point: 260° C.
(f) filler other than non-crosslinkable (meth)acrylate polymer
FASG: fluoroaluminosilicate glass powder, average particle size (D50): 10 μm The method for producing an artificial tooth was as follow: (a), (c), (e) and (d) were mixed at a compounding ratio recited in Table 10 to provide a liquid component, and (b) and (f) were mixed to provide a powder component; the liquid component and the powder component were mixed so that the compounding ratio recited in Table 10 was obtained, and an artificial tooth-shaped mold was filled with the resulting mixture and heated at 100° C. for 1 minute; and the resultant was left to be cooled to provide an artificial tooth.

TABLE 10

| | Composition | Example 42 | Example 43 | Example 44 | Example 45 | Example 46 | Example 47 | Example 48 | Example 49 |
|---|---|---|---|---|---|---|---|---|---|
| (a) | MMA | 100 | 100 | 100 | 100 | 100 | 100 | 100 | 100 |
| (e) | EMA | | | | | | | | |
| (b) | PMMA(1) | 200 | | 100 | 190 | | | | |
| | PMMA(2) | | 200 | 100 | | 200 | 200 | 200 | 200 |
| (f) | FASG | | | | 10 | | | | |
| (c) (Outer percentage) | BPO | 0.2 | 0.2 | 0.2 | 0.2 | 0.2 | 0.2 | 0.2 | 0.2 |
| (d) (Outer percentage) | α-Terpinene | 0.5 | 0.5 | 0.5 | 0.5 | | | | |
| | β-Terpinene | | | | | | 0.5 | | |
| | γ-Terpinene | | | | | | | 0.1 | 0.3 | 0.5 |
| | Total | 200.7 | 300.7 | 300.7 | 300.7 | 300.7 | 300.3 | 300.5 | 300.7 |

TABLE 10-continued

| Test items | Cracks | ⊙ | ⊙ | ⊙ | ⊙ | ⊙ | ⊙ | ○ | ⊙ |
|---|---|---|---|---|---|---|---|---|---|
| | Foaming | ○ | ⊙ | ○ | ○ | ⊙ | ⊙ | ⊙ | ⊙ |
| | Local shrinkage | ○ | ○ | ○ | ○ | ⊙ | ○ | ⊙ | ⊙ |
| | Vickers hardness | 20.3 | 19.7 | 20.1 | 19.8 | 19.7 | 20.4 | 20 | 19.9 |

| | Composition | Example 50 | Example 51 | Example 52 | Example 53 | Example 54 | Example 55 | Comparative Example 7 |
|---|---|---|---|---|---|---|---|---|
| (a) | MMA | 100 | 100 | 100 | 100 | 100 | | 100 |
| (e) | EMA | | 10 | 20 | 20 | 20 | 100 | |
| (b) | PMMA(1) | | | | 100 | | | |
| | PMMA(2) | 200 | 200 | 200 | | 300 | 200 | 200 |
| (f) | FASG | | | | | | | |
| (c) (Outer percentage) | BPO | 0.2 | 0.2 | 0.2 | 0.2 | 0.2 | 0.2 | 0.2 |
| (d) (Outer percentage) | α-Terpinene | | | | | | | |
| | β-Terpinene | | | | | | | |
| | γ-Terpinene | 3 | 1 | 0.5 | 0.5 | 0.5 | 0.5 | |
| | Total | 303.2 | 311 | 320.7 | 220.7 | 420.7 | 300.7 | 300.2 |
| Test items | Cracks | ⊙ | ○ | ○ | ⊙ | ⊙ | Δ | ○ |
| | Foaming | ⊙ | ⊙ | ⊙ | ○ | ⊙ | ⊙ | X |
| | Local shrinkage | ⊙ | ○ | ⊙ | ⊙ | ⊙ | Δ | Δ |
| | Vickers hardness | 16.7 | 20.1 | 19.9 | 203 | 19.7 | 17.2 | 20.2 |

(parts by weight)

In each of Examples 42 and 43, the difference in the type of the non-crosslinkable (meth)acrylate polymer (polymethyl methacrylate powder) (b) was examined, and problematic defects such as cracks, foaming and local shrinkage were not observed even when any of the polymethyl methacrylate powders was used.

Example 44 was a system in which a plurality of the non-crosslinkable (meth)acrylate polymers (polymethyl methacrylate powders) (b) were combined and added, and foaming and local shrinkage were slightly observed and no cracks were observed.

In Example 45, a filler other than the non-crosslinkable (meth)acrylate polymer being Component (b) was added as Component (f) to the non-crosslinkable (meth)acrylate polymer (polymethyl methacrylate powder) (b), and foaming and local shrinkage were slightly observed and no cracks were observed.

In each of Examples 43, 46 and 49, the difference in the type of the chain transfer agent was examined, and generation of cracks and foaming were not observed even when any of the chain transfer agents was used.

In each of Examples 47, 48, 49 and 50, and Comparative Example 7, the amount of the chain transfer agent to be added was examined. While generation of cracks and local shrinkage were only slightly observed in each of Examples 47, 48, 49 and 50, inner foaming was observed too much in Comparative Example 7 because the chain transfer agent (d) was not added.

Examples 51 and 52 were a system in which a polymerizable monomer other than Component (a) was added as Component (e) to the monofunctional polymerizable monomer. In each case, generation of cracks and local shrinkage were only slightly observed.

In each of Examples 53 and 54, the compounding ratio of the liquid material composition to the powder material composition was examined. In Example 53, foaming was only slightly observed. In Example 54, it was confirmed that molding could be conducted without any problem.

With respect to the surface hardness (physical property) in each of Examples 42 to 54 and Comparative Example 7, while the surface hardness was observed to tend to be slightly deteriorated in Example 50 in which the chain transfer agent (d) was added in an amount of 3 parts by weight based on 100 parts by weight of Component (a), such deterioration was considered not to be problematic and therefore it could be determined that there was no influence on the surface hardness (physical property) depending on the presence of addition of the chain transfer agent.

In Example 55, Component (a) was entirely replaced with Component (e) in the component composition in each of Examples. In Example 55, cracks and local shrinkage were confirmed to be generated.

What is claimed is:

1. A dental curable composition for a resin material for dental cutting and machining comprising:
   (a) a polymerizable monomer and (b) a filler in a weight ratio of 10:90 to 70:30, and 0.01 to 10 parts by weight of (c) a polymerization initiator and 0.1 to 0.5 part by weight of (d) a chain transfer agent being a terpenoid compound based on 100 parts by weight of the polymerizable monomer (a),
   wherein the polymerization initiator (c) consists of a thermal polymerization initiator,
   wherein an average particle size of the filler (b) is in a range from 0.5 to 100 μm,
   wherein the filler (b) consists of a member selected from the group consisting of an inorganic filler, a polyvinyl acetate, a polyethylene glycol, a polypropylene glycol, a polyvinyl alcohol, and combinations thereof, and
   wherein the dental curable composition is:
   a two part dental curable composition wherein neither of the two parts is a powder component containing the polymerization initiator (c).

2. The dental curable composition according to claim 1, wherein the dental curable composition comprises 0.1 to 5 parts by weight of the polymerization initiator (c) based on 100 parts by weight of the polymerizable monomer (a).

3. The dental curable composition according to claim 1, wherein the dental curable composition comprises 0.1 to 2 parts by weight of the polymerization initiator (c) based on 100 parts by weight of the polymerizable monomer (a).

4. The dental curable composition according to claim 1, wherein the thermal polymerization initiator is an organic peroxide and/or an azo compound.

5. The dental curable composition according to claim 1, wherein the thermal polymerization initiator is at least one thermal polymerization initiator selected from a group consisting of benzoyl peroxide, p-chlorobenzoyl peroxide, 2,4-dichlorobenzoyl peroxide, acetyl peroxide, lauroyl peroxide, tert-butyl peroxide, cumene hydroperoxide, 2,5-dimethylhexane, 2,5-dihydroperoxide, methyl ethyl ketone peroxide, tert-butylperoxybenzoate, azobisisobutyronitrile, azobis(methyl isobutyrate) and azobiscyanovaleric acid.

6. The dental curable composition according to claim 1, wherein the thermal polymerization initiator is at least one thermal polymerization initiator selected from a group consisting of benzoyl peroxide, p-chlorobenzoyl peroxide, 2,4-dichlorobenzoyl peroxide, acetyl peroxide, lauroyl peroxide, tert-butyl peroxide, cumene hydroperoxide, 2,5-dimethylhexane, 2,5-dihydroperoxide, methyl ethyl ketone peroxide and tert-butylperoxybenzoate.

7. The dental curable composition according to claim 1, wherein the thermal polymerization initiator is at least one thermal polymerization initiator selected from a group consisting of azobisisobutyronitrile, azobis(methyl isobutyrate) and azobiscyanovaleric acid.

8. The dental curable composition according to claim 1, wherein the chain transfer agent (d) is at least one of α-terpinene, β-terpinene and γ-terpinene.

9. A composite resin artificial tooth having a multilayer structure comprising:
at least one composite resin layer produced by a dental curable composition comprising:
(a) a polymerizable monomer and (b) a filler in a weight ratio of 10:90 to 70:30, and 0.01 to 10 parts by weight of (c) a polymerization initiator and 0.001 to 1 part by weight of (d) a chain transfer agent being a terpenoid compound based on 100 parts by weight of the polymerizable monomer (a),
wherein the polymerization initiator (c) consists of a thermal polymerization initiator,
wherein an average particle size of the filler (b) is in a range from 0.5 to 100 μm,
wherein the filler (b) consists of a member selected from the group consisting of an inorganic filler, a polyvinyl acetate, a polyethylene glycol, a polypropylene glycol, a polyvinyl alcohol, and combinations thereof, and
wherein the dental curable composition is:
a one part dental curable composition, or
a two part dental curable composition wherein neither of the two parts is a powder component containing the polymerization initiator (c); and
at least one acrylic resin layer comprising:
(e) a monofunctional (meth)acrylate polymerizable monomer,
(f) a non-crosslinkable (meth)acrylate polymer,
(c) a polymerization initiator, and
(d) a chain transfer agent.

10. The composite resin artificial tooth according to claim 9, wherein the composite resin artificial tooth is prepared by molding and processing with pressure and heat in a mold.

11. A composite resin artificial tooth having a multilayer structure comprising a composite resin layer produced by a dental curable composition comprising:
(a) a polymerizable monomer and (b) a filler in a weight ratio of 10:90 to 70:30, and 0.01 to 10 parts by weight of (c) a polymerization initiator and 0.001 to 1 part by weight of (d) a chain transfer agent being a terpenoid compound based on 100 parts by weight of the polymerizable monomer (a),
wherein the polymerization initiator (c) consists of a thermal polymerization initiator,
wherein the filler (b) consists of a member selected from the group consisting of an inorganic filler, a polyvinyl acetate, a polyethylene glycol, a polypropylene glycol, a polyvinyl alcohol, and combinations thereof, and
wherein the structure comprises:
at least one of the composite resin layer; and
at least one acrylic resin layer comprising:
(e) a monofunctional (meth)acrylate polymerizable monomer,
(f) a non-crosslinkable (meth)acrylate polymer,
(c) a polymerization initiator, and
(d) a chain transfer agent.

12. The composite resin artificial tooth according to claim 11, wherein the composite resin artificial tooth is molded in a mold.

* * * * *